US011987616B2

(12) United States Patent
Grigoryan et al.

(10) Patent No.: US 11,987,616 B2
(45) Date of Patent: May 21, 2024

(54) ANTIGEN BINDING MOLECULES TARGETING SARS-CoV-2

(71) Applicant: Flagship Pioneering Innovations VI, LLC, Cambridge, MA (US)

(72) Inventors: Gevorg Grigoryan, Arlington, MA (US); John Ingraham, Cambridge, MA (US)

(73) Assignee: Flagship Pioneering Innovations VI, LLC, Cambridge, MA (US)

( * ) Notice: Subject to any disclaimer, the term of this patent is extended or adjusted under 35 U.S.C. 154(b) by 0 days.

(21) Appl. No.: 18/169,464

(22) Filed: Feb. 15, 2023

(65) Prior Publication Data

US 2023/0287089 A1    Sep. 14, 2023

Related U.S. Application Data

(63) Continuation of application No. PCT/US2021/047757, filed on Aug. 26, 2021.

(60) Provisional application No. 63/070,707, filed on Aug. 26, 2020.

(51) Int. Cl.
*C07K 16/10* (2006.01)
*A61P 31/14* (2006.01)
*A61K 39/00* (2006.01)

(52) U.S. Cl.
CPC ............. *C07K 16/10* (2013.01); *A61P 31/14* (2018.01); *A61K 39/00* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 8,088,376 B2 | 1/2012 | Chamberlain et al. |
| 8,394,925 B2 | 3/2013 | Chamberlain et al. |
| 8,546,543 B2 | 10/2013 | Lazar |
| 9,803,023 B2 | 10/2017 | Chamberlain et al. |
| 10,336,818 B2 | 7/2019 | Chamberlain et al. |
| 10,787,501 B1 | 9/2020 | Babb et al. |
| 11,028,167 B1 | 6/2021 | Glanville et al. |
| 11,168,128 B2 | 11/2021 | Corti et al. |
| 11,192,940 B2 | 12/2021 | Walker et al. |
| 2015/0152183 A1 | 6/2015 | Chamberlain et al. |
| 2016/0046720 A1 | 2/2016 | Sato et al. |
| 2019/0119407 A1 | 4/2019 | Hsu et al. |
| 2021/0214431 A1 | 7/2021 | Rommelaere et al. |
| 2021/0261650 A1 | 8/2021 | Corti et al. |
| 2021/0277095 A1 | 9/2021 | Chamberlain et al. |
| 2022/0089752 A1 | 3/2022 | Liu et al. |
| 2022/0112307 A1 | 4/2022 | Chamberlain et al. |
| 2022/0403009 A1 | 12/2022 | Hinton et al. |
| 2023/0058162 A1 | 2/2023 | Hinton et al. |
| 2023/0174628 A1 | 6/2023 | Xie et al. |
| 2023/0279081 A1 | 9/2023 | Grigoryan et al. |
| 2023/0295275 A1 | 9/2023 | Grigoryan et al. |
| 2023/0357366 A1 | 11/2023 | Borriello et al. |
| 2023/0357367 A1 | 11/2023 | Borriello et al. |

FOREIGN PATENT DOCUMENTS

| | | |
|---|---|---|
| EP | 2235059 B1 | 2/2015 |
| EP | 2444423 B1 | 3/2015 |
| EP | 3031913 A1 | 6/2016 |
| EP | 2808343 B1 | 5/2019 |
| EP | 3872091 A1 | 9/2021 |
| EP | 3138853 B1 | 11/2021 |
| EP | 4147716 A1 | 3/2023 |
| EP | 4188951 A2 | 6/2023 |
| WO | 2005/012360 A2 | 2/2005 |
| WO | 2005/054469 A1 | 6/2005 |
| WO | 2006/051091 A1 | 5/2006 |
| WO | 2006/053301 A2 | 5/2006 |
| WO | 2009/058492 A2 | 5/2009 |
| WO | 2009/086320 A1 | 7/2009 |
| WO | 2016/050889 A1 | 4/2016 |
| WO | 2021/156490 A2 | 8/2021 |
| WO | 2021/158521 A1 | 8/2021 |
| WO | 2021/173753 A1 | 9/2021 |
| WO | 2021/186190 A1 | 9/2021 |
| WO | 2021/203053 A1 | 10/2021 |
| WO | 2021/207152 A1 | 10/2021 |
| WO | 2021/211775 A1 | 10/2021 |
| WO | 2021/226560 A1 | 11/2021 |
| WO | 2021/247925 A1 | 12/2021 |

(Continued)

OTHER PUBLICATIONS

Vajdos et al. (J Mol Biol. Jul. 5, 2002;320(2):415-28). (Year: 2002).*
Bedouelle et al. (FEBS J. Jan. 2006;273(1):34-46). (Year: 2006).*
Brown et al. (J Immunol. May 1, 1996;156(9):3285-91). (Year: 1996).*
Colman (Research in Immunology, 145:33-36, 1994). (Year: 1994).*
Rudikoff et al. (Proc. Natl. Acad. Sci. USA, 79: 1979-1983, Mar. 1982). (Year: 1982).*
Esparza, T.J. and Brody, D.L., "High Affinity Nanobodies Block SARS-CoV-2 Spike Receptor Binding Domain Interaction with Human Angiotensin Converting Enzyme," bioRxiv, Retrieved from Internet URL: https://www.biorxiv.org/content/10.1101/2020.07.24.219857v1.full.pdf; 15 Pages (2020).

(Continued)

*Primary Examiner* — Zachary S Skelding
(74) *Attorney, Agent, or Firm* — Hamilton, Brook, Smith & Reynolds, P.C.

(57) ABSTRACT

The invention provides, in various embodiments, polypeptides (e.g., camelid antibodies and antigen binding fragments thereof) that specifically bind to Spike glycoprotein of severe acute respiratory syndrome coronavirus (e.g., SARS-CoV-2-Spike). The invention also provides, in various embodiments, fusion proteins comprising one or more of the polypeptides, polynucleotides encoding the polypeptides, vectors and host cells suitable for expressing the polypeptides, and methods for treating viral infections (e.g., COVID-19).

27 Claims, 4 Drawing Sheets

Specification includes a Sequence Listing.

(56) References Cited

FOREIGN PATENT DOCUMENTS

| WO | 2022/010912 A1 | 1/2022 |
|---|---|---|
| WO | 2022/010921 A1 | 1/2022 |
| WO | 2022/015573 A2 | 1/2022 |
| WO | 2022/026475 A2 | 2/2022 |
| WO | 2022/046888 A1 | 3/2022 |
| WO | 2022/047033 A1 | 3/2022 |
| WO | 2022/140845 A1 | 7/2022 |
| WO | 2022/159685 A2 | 7/2022 |
| WO | 2022/204202 A1 | 9/2022 |
| WO | 2022/251119 A2 | 12/2022 |
| WO | 2022/271863 A1 | 12/2022 |
| WO | 2023/028603 A2 | 3/2023 |
| WO | 2023/037119 A1 | 3/2023 |
| WO | 2023/215910 A1 | 11/2023 |

OTHER PUBLICATIONS

GenBank, "Lama glama immunoglobulin heavy chain variable region mRNA, partial cds," Database accession No. MT350284; 2 Pages (2020).
Huo, J. et al., "Neutralizing nanobodies bind SARS-CoV-2 spike RBD and block interaction with ACE2," Nature Structural and Molecular Biology, vol. 27; 846-854 (2020).
Schoof, M. et al., "An ultra-potent synthetic nanobody neutralizes SARS-CoV-2 by locking Spike into an inactive conformation," bioRxiv, Retrieved from Internet URL: https://www.biorxiv.org/content/10.1101.2020.08.08.238469v2.full.pdf; 24 Pages (2020).
Wrapp, D. et al., "Structural Basis for Potent Neutralization of Betacoronaviruses by Single-Doman Camelid Antibodies," Cell, vol. 181; 1004-1015 (2020).
Wu, Y. et al., "Identification of Human Single-Domain Antibodies against SARS-CoV-2," Cell Host & Microbe, vol. 27; 891-898 (2020).
Xiang, Y. et al., "Versatile, Multivalent Nanobody Cocktails Efficiently Neutralize SARS-CoV-2," bioRxiv, Retrieved from Internet URL: https://www.biorxiv.org/content/10.1101.2020.08.24.264333v3.full.pdf; 34 Pages (2020).
Zupancic, J.M. et al., "Engineered Multivalent Nanobodies Potently and Broadly Neutralize SARS-CoV-2," Advanced Therapeutics, vol. 4; 2100099; 9 Pages (2021).
Notification of Transmittal of the International Search Report and the Written Opinion for International Application No. PCT/US2021/047757, dated Dec. 2, 2021.
Baden, L.R. Rubin, E.J., "Covid-19—The Search for Effective Therapy," The New England Journal of Medicine, DOI: 10.1056/NEJMe2005477; 2 pages (2020).
Baud, D. et al., "Real estimates of mortality following COVID-19 infection," The Lancet, S1473-3099(20)30234-6; 773-774 (2020).
International Preliminary Report on Patentability received for PCT Patent Application No. PCT/US21/47757, dated Mar. 9, 2023, 9 pages.
Kunik, V. et al., "Paratome: an online tool for systematic identification of antigen-binding regions in antibodies based on sequence or structure," Nucleic Acids Research, vol. 40; W521-W524 (2012).
Needleman, S.B. and Wunsch, C.D., "A General Method Applicable to the Search for Similarities in the Amino Acid Sequence of Two Proteins," J. Mol. Biol., vol. 48; 443-453 (1970).
Pearson, W.R. and Lipman, D.J., "Improved tools for biological sequence comparison," Proc. Natl. Acad. Sci., vol. 85; 2444-2448 (1988).
Smith, T.F. and Waterman, M.S., "Comparison of Biosequences," Advances in Applied Mathematics, vol. 2; 482-489 (1981).
Wrapp, D. et al., "Crystal structure of the SARS-CoV-1 RBD bound by the cross-reactive single-domain antibody SARS VHH-72," Protein Data Bank (PDB) Accession No. 6WAQ, retrieved from internet URL: https://www.rcsb.org/structure/6waq; Retrieved on Sep. 15, 2023; 5 pages.
Ziegler, C.G.K. et al., "SARS-CoV-2 Receptor ACE2 Is an Interferon-Stimulated Gene in Humane Airway Epithelial Cells and is Detected in Specific Cell Subsets Across Tissues," Cell, vol. 181; 1016-1035 (2020).
Mahoney, K et al., "1363. Preliminary Safety Results from a Phase 1 First in Human Study of VYD222: an Extended Half-Life Monoclonal Antibody (mAb) in Development for COVID-19 Prevention," Open Forum Infect Dis. Nov. 2, 20237;10(Suppl 2):ofad500.1200. doi: 10.1093/ofid/ofad500.1200. PMCID: PMC10678193.
Markovic, I. and Savvides, S., "Modulation of Signaling Mediated by TSLP and IL-7 in Inflammation, Autoimmune Diseases, and Cancer," Frontiers in Immunology, vol. 11; Art. 1557; 19 pages (2020).
Martinez, D.R. et al., "A broadly cross-reactive antibody neutralizes and protects against sarbecovirus challenge in mice," Sci. Transl. Med., 10.1126/scitranslmed.abj7125; Jan. 2, 20226; 14(629): eabj7125; 18 pages.
McCallum, M. et al., "Structural basis of SARS-CoV-2 Omicron immune evasion and receptor engagement," bioRxiv, 27 pages (2021).
McMahan, K. et al., "Correlates of protection against SARS-CoV-2 in rhesus macaques," Nature, vol. 590(7847); 630-634; Supp'l Data included (2021).
McNeilly AS et al., The differential secretion of FSH and LH: regulation through genes, feedback and packaging. Reprod Suppl. 2003;61:463-76. PMID: 14635955.
Melanie, P. et al., "Modeling brings additional insights into the kinetics of SARS-CoV-2 neutralizing antibody," MedRxiv; https://doi.org/10.1101/2021.10.13.21264693; 4 pages (2021).
Menzies-Gow, A. et al., "Tezepelumab in Adults and Adolescents with Severe, Uncontrolled Asthma," N Eng J Med, vol. 384; 1800-1809 (2021).
Menzies-Gow, A. et al., "Unmet need in severe, uncontrolled asthma: can anti-TSLP therapy with tezepelumab provide a valuable new treatment option?," Respiratory Research, vol. 21(1); 268; 7 pages (2020).
Meyer, M.C. et al., "Development Approach for Anti-Spike Monoclonal Antibodies to Keep Pace with SARS-CoV-2 Variants," EMA-FDA Workshop: Efficacy of monoclonal antibodies in the context of rapidly evolving SARS-CoV-2 variants, Presentation; 10 pages (2022).
Miller, J. et al., "Substantial Neutralization Escape by the SARS-CoV-2 Omicron Variant BQ.1.1," bioRxiv, https://doi.org/10.1101/2022.11.01.514722; 17 pages (2022).
Montgomery, H. et al., "Efficacy and safety of intramuscular administration of tixagevimab-cilgavimab for early outpatient treatment of COVID-19 (TACKLE): a phase 3, randomised, double-blind, placebo-controlled trial," Lancet Respir Med, https://doi.org/10.1016/S2213-2600(22)00180-1; 206 pages; The Protocol (2022).
Montgomery, H. et al., "Efficacy and safety of intramuscular administration of tixagevimab-cilgavimab for early outpatient treatment of COVID-19 (TACKLE): a phase 3, randomised, double-blind, placebo-controlled trial," Lancet Respir Med, vol. 10(10); 985-996; doi: 10.1016/S2213-2600(22)00180-1; Epub Jun. 7, 2022. PMID: 35688164; PMCID: PMC9173721; 12 pages (2022).
Moulana A et al., Compensatory epistasis maintains ACE2 affinity in SARS-CoV-2 Omicron BA.1. Nat Commun. Nov. 16, 2022;13(1):7011. doi: 10.1038/s41467-022-34506-z. PMID: 36384919; PMCID: PMC9668218.
Muñoz-Fontela C et al., Advances and gaps in SARS-CoV-2 infection models. PLoS Pathog. Jan. 13, 2022;18(1):e1010161. doi: 10.1371/journal.ppat. 1010161. PMID: 35025969; PMCID: PMC8757994.
Nader A et al., Pharmacokinetics, Safety, and Tolerability of Anti-SARS-CoV-2 Monoclonal Antibody, Sotrovimab, Delivered Intravenously or Intramuscularly in Japanese and Caucasian Healthy Volunteers. Clin Pharmacokinet. Jan. 2024;63(1):57-68. doi: 10.1007/s40262-023-01319-2. Epub Nov. 13, 2023. PMID: 37955825; PMCID: PMC10786731.
Naldini L et al., Efficient transfer, integration, and sustained long-term expression of the transgene in adult rat brains injected with a lentiviral vector. Proc Natl Acad Sci U S A. Oct. 15, 1996;93(21):11382-8. doi: 10.1073/pnas.93.21.11382. PMID: 8876144; PMCID: PMC38066.
Narkhede, Y.B. et al., "Targeting Viral Surface Proteins through Structure-Based Design," Viruses, vol. 13; 1320; 18 pages (2021).

(56) References Cited

OTHER PUBLICATIONS

Nicol L et al., Differential secretion of gonadotrophins: investigation of the role of secretogranin II and chromogranin A in the release of LH and FSH in LbetaT2 cells. J Mol Endocrinol. Apr. 2004;32(2):467-80. doi: 10.1677/jme.0.0320467. PMID: 15072552.
Nih COVID-19 Treatment Guidelines: Anti-SARS-CoV-2 Monoclonal Antibodies: http://www.covid19treatmentguidelines.nih.gov/therapies/anti-sars-cov-2-antibody-products/anti-sars-cov-2-monoclonal-antibodies (date unavailable).
O'Brien, M.P. et al., "Subcutaneous REGEN-COV Antibody Combination to Prevent Covid-19," The New England Journal of Medicine, vol. 385(13); 1184-1195 (2021).
Ozawa, H et al., "The Granin Family-Its Role in Sorting and Secretory Granule Formation," Cell Structure and Function, vol. 20; 415-420 (1995).
Pantaleo, G. et al., "Antibodies to combat viral infections: development strategies and progress," Nat Rev Drug Discov., Sep. 2022;21(9):676-696. doi: 10.1038/s41573-022-00495-3. Epub Jun. 20, 2022. PMID: 35725925; PMCID: PMC9207876.
Park, T. et al., "Spike protein binding prediction with neutralizing antibodies of SARS-CoV-2" retrieved from Internet URL: http://www.biorxiv.org/content/10.1101/2020.02.22.951178v1.full.pdf; 22 Pages; Retrieved on Jun. 9, 2021.
Park, Y. et al., "Antibody-mediated broad sarbecovirus neutralization through ACE2 molecular mimicry," Science, 10.1126/science.abm8143; 14 pages (2022).
Park, Y. et al., "Imprinted antibody responses against SARS-CoV-2 Omicron sublineages," bioRxiv, 68 pages (2022).
Perez, J.L., "Use of neutralizing antibody or PK/IC50 threshold to expedite clinical development for prophylactic monoclonal antibodies," EMA/FDA workshop on monoclonal antibodies against SARS-CoV-2, AstraZeneca, Vaccines & Immune Therapies Unit; Presentation; 6 pages (2022).
Pérez-Vargas J et al., Discovery of lead natural products for developing pan-SARS-CoV-2 therapeutics. Antiviral Res. Jan. 2023;209:105484. doi: 10.1016/j.antiviral.2022.105484. Epub Dec. 8, 2022. Erratum in: Antiviral Res. May 2023;213:105577. PMID: 36503013; PMCID: PMC9729583.
Petkova SB et al., Enhanced half-life of genetically engineered human IgG1 antibodies in a humanized FcRn mouse model: potential application in humorally mediated autoimmune disease. Int Immunol. Dec. 2006; 18(12):1759-69. doi: 10.1093/intimm/dxl110. Epub Oct. 3, 20061. PMID: 17077181.
Pinto et al. "Cross-neutralization of SARS-CoV-2 by a human monoclonal SARS-CoV antibody", Nature 583(7815): 290-95 (2020).
Pinto, D. et al., "Broad betacoronavirus neutralization by a stem helix-specific human antibody," Science, Supplemental Materials, 37 pages (2021).
Pinto, D. et al., "Structural and functional analysis of a potent sarbecovirus neutralizing antibody," Retrieved from Internet URL: http://www.biorxiv.org/content/10.1101.2020.04.07.023903v3.full.pdf; 28 pages; Retrieved on Apr. 10, 2020.
Pinto, D., et al., "Broad betacoronavirus neutralization by a stem helix-specific human antibody", Coronavirus, vol. 373, No. 6559, Sep. 3, 2021, pp. 1109-1116.
Planas, D. et al., "Reduced sensitivity of SARA-CoV-2 variant Delta to antibody neutralization," Nature, 22 pages (2021).
Polack, F.P. et al., "Safety and Efficacy of the BNT162b2 mRNA Covid-19 Vaccine," N. Engl. J. Med, vol. 383; No. 27; 2603-2615 (2020).
Portal-Celhay, C. et al., "Phase 2 dose-ranging study of the virologic efficacy and safety of the combination Covid-19 antibodies casirivimab and imdevimab in the outpatient setting," medRxiv; https://doi.org/10.1101/2021.11.09.21265912; 35 pages (2021).
Pradhan, A. et al., "Affinity maturation of cross-reactive CR3022 antibody against the receptor binding domain of SARS-CoV-2 via in silico site-directed mutagenesis," Retrieved from Internet URL: http://assets.researchsquare.com/files/rs-92745/v1/60243c22-34a9-439c-89cb-d45b2b46b396.pdf?c=1631858249; 10 pages; Retrieved on Oct. 5, 2021.
Prévost J et al., Cross-Sectional Evaluation of Humoral Responses against SARS-CoV-2 Spike. Cell Rep Med. Oct. 20, 2020;1(7):100126. doi: 10.1016/j.xcrm.2020.100126. Epub Sep. 3, 20200. PMID: 33015650; PMCID: PMC7524645.
Pymm, P. et al., "Nanobody cocktails potently neutralize SARS-CoV-2 D614G N501Y variant and protect mice," PNAS, vol. 118; No. 19; e2101918118, 12 pages (2021).
Quanterix, The Science of Precision Health, "Simoa® SARS CoV-2 N Protein Advantage Kit: HD-X Data Sheet," Quanterix Corporation, Doc Template-0061 03; DS-0528 01DS-0528; 2 pages (2020).
Quanterix, The Science of Precision Health, "Simoa® SARS-CoV-2 Spike IgG Advantage Kit: HD-X Data Sheet," Quanterix Corporation, Doc Template-0061 03; DS-0521 01DS-0521; 3 pages (2020).
Rambaut, A. et al., "A dynamic nomenclature proposal for SARSCoV-2 lineages to assist genomic epidemiology," Nat Microbiol., vol. 5; No. 11; 1403-1407 (2020).
Rappazzo CG et al., Broad and potent activity against SARS-like viruses by an engineered human monoclonal antibody. Science. Feb. 19, 2021;371(6531):823-829. doi: 10.1126/science.abf4830. Epub Jan. 25, 2021. PMID: 33495307; PMCID: PMC7963221.
Rockett, R. et al., "Resistance Mutations in SARS-CoV-2 Delta Variant after Sotrovimab Use," N Engl J Med, vol. 386; No. 15; 4 pages (2022).
Rudikoff, S., et al., "Single amino acid substitution altering antigen-binding specificity.", Proceedings Of The National Academy Of Sciences, National Academy Of Sciences, vol. 79, Mar. 1, 1982, pp. 1979-1983.
Rujas, E. et al., "Multivalency transforms SARS-CoV-2 antibodies into ultrapotent neutralizers," Nature Communications, vol. 12(1); 3661; 12 pages (2021).
Sauer, M. M., et al., "Structural basis for broad coronavirus neutralization", Nature Structural & Molecular Biology, vol. 28, 2021, pp. 478-486.
Saunders, K.O., "Conceptual Approaches to Modulating Antibody Effector Functions and Circulation Half-Life," Front Immunol., vol. 10; 1296 (2019).
Saunders, K.O., "Developing a Neutralizing Antibody Vaccine for Pandemic and Pre-Emergent Coronaviruses," Duke University School of Medicine, IDWeek, 31 pages (2023).
Schepens, B. et al., "An affinity-enhanced, broadly neutralizing heavy chain-only antibody protects against SARS-CoV-2 infection in animal models," Sci Transl Med., vol. 13; eabi7826; 18 pages (2021).
Davenport, M., "Correlates of protection using a neutralisation approach," Kirby Institute, 25 pages (2022).
Davis-Gardner, M.E. et al., "mRNA bivalent booster enhances neutralization against BA.2.75.2 and BQ.1.1," bioRxiv; https://doi.org/10.1101/2022.10.31.514636; 7 pages (2022).
De Gasparo, R.D. et al., "Bispecific IgG neutralizes SARS-CoV-2 variants and prevents escape in mice," Nature, vol. 593(7859); 424-428 (2020).
De Genst et al., "Anti body repertoire development in camelids" Dev Comp Immunol; 30:187-98 (2006).
Dejnirattisai, W. et al., "The antigenic anatomy of SARS-CoV-2 receptor binding domain," Cell, vol. 184; 2183-2200 (2021).
Dings C et al., Pharmacometric Modeling of the Impact of Azelastine Nasal Spray on SARS-CoV-2 Viral Load and Related Symptoms in Covid-19 Patients. Pharmaceutics. Sep. 27, 2022;14(10):2059. doi: 10.3390/pharmaceutics 14102059. PMID: 36297492; PMCID: PMC9609097.
Divine, R. et al., "Designed proteins assemble antibodies into modular nanocages," Science, vol. 372(6537); No. 47; 17 pages (2021).
Dougan, M. et al., "A randomized, placebo-controlled clinical trial of bamlanivimab and etesevimab together in high-risk ambulatory patients with COVID-19 and validation of the prognostic value of persistently high viral load," Oxford University Press for the Infectious Diseases Society of America; 29 pages (2021).
Dougan, M. et al., "Bebtelovimab, alone or together with bamlanivimab and etesevimab, as a broadly neutralizing monoclonal antibody treatment for mild to moderate, ambulatory COVID-19," medRxiv, 33 pages (2022).

(56) References Cited

OTHER PUBLICATIONS

Dube, S. et al., "Fully vaccinated individuals with immunocompromised conditions are still at increased risk of severe COVID-19 outcomes from the Omicron variant: initial results from INFORM, a retrospective health database observational study in England," Presented at IDWeek (Abstract 1096); Oct. 11-15, 2023; Boston, Massachusetts, USA; 20 pages.

Durán-Pastén ML & Fiordelisio T. GnRH-Induced Ca(2+) Signaling Patterns and Gonadotropin Secretion in Pituitary Gonadotrophs. Functional Adaptations to Both Ordinary and Extraordinary Physiological Demands. Front Endocrinol (Lausanne). Sep. 30, 2013;4:127. doi: 10.3389/fendo.2013.00127. PMID: 24137156; PMCID: PMC3786263.

Edara VV et al., Neutralizing Antibodies Against SARS-CoV-2 Variants After Infection and Vaccination. JAMA. May 11, 2021;325(18): 1896-1898. doi: 10.1001/jama.2021.4388. PMID: 33739374; PMCID: PMC7980146.

EMA website. CHMP Assessment Report for Sotrovimab, Dec. 2021. Updated Jan. 12, 2023. Accessed May 22, 2023. https://www.ema.europa.eu/en/documents/assessmentreport/xevudy-epar-public-assessment-report_en.pdf.

European Cancer Patient Coalition (ECPC). Joint statement on the protection of immunocompromised patients during the Covid-19 pandemic. Updated Jul. 7, 2022. Accessed Feb. 17, 2023. https://ecpc.org/joint-statement-on-the-protection-ofimmunocompromised-patients/.

European Medicines Agency, Assessment Report, Evusheld, 155 pages (2022).

European Medicines Agency, CHMP Assessment Report for Xevudy; 120 pages (2021).

Eyal, N. et al., "Human Challenge Studies to Accelerate Coronavirus Vaccine Licensure," The Journal of Infectious Diseases, vol. 221; 1752-1756 (2020).

Fact Sheet for Health Care Providers, Bamlanivimab and Etesevimab, Eli Lilly and Company, 45 pages (2021).

Fact Sheet for Health Care Providers, casirivimab and imdevimab, Regeneron Pharmaceuticals, Inc, 54 pages (2021).

Fact Sheet for Health Care Providers, Sotrovimab, GlaxoSmithKline LLC, 37 pages (2022).

FDA Briefing Document, "Bezlotoxumab Injection, Meeting of the Antimicrobial Drugs Advisory Committee (AMDAC)" 29 pages (2016).

FDA Briefing Document, "Vaccines and Related Biological Products Advisory Committee Meeting," EUA amendment request for use of the Moderna Covid-19 Vaccine in children 6 months through 17 years of age, 190 pages (2022).

Fedry, J. et al., "Structural insights into the cross-neutralization of SARS-CoV and SARS-CoV-2 by the human monoclonal antibody 47D11," Sci. Adv., vol. 7(23); eabf5632, 11 pages (2021).

Fenwick, C. et al., "A highly potent antibody effective against SARS-CoV-2 variants of concern," Cell Reports, vol. 37(2); 109814; 19 pages (2021).

Fenwick, C. et al., "Patient-derived monoclonal antibody neutralizes SARS-CoV-2 Omicron variants and confers full protection in monkeys," Nature Microbiology, 33 pages (2022).

Follmann D et al., Examining protective effects of SARS-CoV-2 neutralizing antibodies after vaccination or monoclonal antibody administration. Nat Commun. Jun. 1, 20237;14(1): 23 pages; Supplemental Materials.

Follmann D et al., Examining protective effects of SARS-CoV-2 neutralizing antibodies after vaccination or monoclonal antibody administration. Nat Commun. Jun. 17, 2023;14(1):3605. doi: 10.1038/s41467-023-39292-w. PMID: 37330602; PMCID: PMC10276829.

Francica, J.R. et al., "The SARS-CoV-2 monoclonal antibody AZD3152 potently neutralises historical and currently circulating variants," Presented at the European Congress of Clinical Microbiology and Infectious Diseases (ECCMID), Poster P2636; Copenhagen, Denmark, Apr. 15-18, 2023.

Francica, J.R. et al., "The SARS-CoV-2 Monoclonal Antibody AZD3152 Potently Neutralizes Historical and Emerging Variants and is Being Developed for the Prevention and Treatment of COVID-19 in High-Risk Individuals," IDWeek 2023, Oct. 11-15, 2023, Boston, MA, USA; Poster.

Gau, B.C. et al., "Oligonucleotide mapping via mass spectrometry to enable comprehensive primary structure characterization of an mRNA vaccine against SARS-CoV-2," Scientific Reports, vol. 13; 9038; 16 pages (2023).

Gauvreau, G.M. et al., "Effects of an Anti-TSLP Antibody on Allergen-Induced Asthmatic Responses," N. Eng J Med, vol. 370; 2102-2110 (2014).

Gilbert PB et al., Immune correlates analysis of the mRNA-1273 COVID-19 vaccine efficacy clinical trial. Science. Jan. 7, 2022;375(6576): 75 pages; Supplemental Material.

Gilbert PB et al., Immune correlates analysis of the mRNA-1273 COVID-19 vaccine efficacy clinical trial. Science. Jan. 7, 2022;375(6576):43-50. doi: 10.1126/science.abm3425. Epub Nov. 23, 2021. PMID: 34812653; PMCID: PMC9017870.

Gilbert, P.B. et al., "A Covid-19 Milestone Attained—A Correlate of Protection for Vaccines," N Engl J Med, vol. 387; No. 24; 2203-2206 (2022).

Gobeil, S. et al., "Structural diversity of the SARS-CoV-2 Omicron spike," bioRxiv; 35 pages (2022).

Gov.Uk, "Winter Coronavirus (COVID-19) Infection Study: estimates of epidemiological characteristics, Dec. 21, 2023," Retrieved from Internet URL: https://www.gov.uk/government/statistics/winter-coronavirus-covid-19-infection . . . ; 14 pages; Retrieved on Dec. 21, 2023.

Greaney AJ et al., Complete Mapping of Mutations to the SARS-CoV-2 Spike Receptor-Binding Domain that Escape Antibody Recognition. Cell Host Microbe. Jan. 13, 2021;29(1):44-57.e9. doi: 10.1016/j.chom.2020.11.007. Epub Nov. 19, 2020. PMID: 33259788; PMCID: PMC7676316.

Greaney, A.J. et al., "Comprehensive mapping of mutations to the SARS-CoV-2 receptor-binding domain that affect recognition by polyclonal human serum antibodies," bioRxiv, 35 pages (2021).

Gruell, H. et al., "Antibody-mediated neutralization of SARS-CoV-2," Immunity, vol. 55(6); 925-944 (2022).

Gupta, A. et al., "Early Treatment for Covid-19 with SARS-CoV-2 Neutralizing Antibody Sotrovimab," N Eng J Med, vol. 385(21); 1941-1950 (2021).

Gupta, A. et al., "Early Treatment for Covid-19 with SARS-CoV-2 Neutralizing Antibody Sotrovimab," N Eng J Med, vol. 385(21); The Protocol; 269 pages (2021).

Gutgsell, A.R. et al., "Biosensor-Enabled Deconvolution of the Avidity-Induced Affinity Enhancement for the SARS-CoV-2 Spike Protein and ACE2 Interaction," Anal Chem, vol. 94; 1187-1194 (2022).

Haagmans, B.L. et al., "SARS-CoV-2 Neutralizing Human Antibodies Protect Against Lower Respiratory Tract Disease in a Hamster Model," Journal of Infectious Diseases, vol. 223(12):2020-2028 (2021).

Hansen, J. et al., "Studies in humanized mice and convalescent humans yield a SARS-CoV-2 antibody cocktail," Science, vol. 369(6506); 1010-1014 (2020).

Haraya, K. et al., "Translational Approach for Predicting Human Pharmacokinetics of Engineered Therapeutic Monoclonal Antibodies with Increased FcRn-Binding Mutations," BioDrugs, vol. 37; No. 1; 99-108 (2023).

Harpaz R. et al., "Prevalence of Immunosuppression Among US Adults, 2013," JAMA, vol. 316; No. 23; 2547-2548 (2016).

Hastie, K.M. et al., "Defining variant-resistant epitopes targeted by SARS-CoV-2 antibodies: A global consortium study," Science, 10.1126/science.abh2315; 13 pages (2021).

Hastie, K.M. et al., "Defining variant-resistant epitopes targeted by SARS-CoV-2 antibodies: A global consortium study," Science, 10.1126/science.abh2315; 13 pages; Supplemental Information (2021).

Hie, B.L. et al., "Efficient evolution of human antibodies from general protein language models," Nature Biotechnology, https://doi.org/10.1038/s41587-023-01763-2; 26 pages (2023).

Highlights of Emergency Use Authorization, Bebtelovimab, 21 pages (2022).

(56) References Cited

OTHER PUBLICATIONS

WHO website. WHO Coronavirus (COVID-19) Dashboard With Vaccination Data. Updated Feb. 17, 2023. Accessed Feb. 19, 2023. https://covid19.who.int/.
Worzner, K. et al., "Adjuvanted SARS-CoV-2 spike protein elicits neutralizing antibodies and CD4 T cell responses after a single immunization in mice," EBioMedicine, vol. 63; 103197; 9 pages (2021).
Wrapp, D., et al., "Cryo-EM structure of the 2019-nCOV spike in the prefusion conformation", Science, vol. 367, No. 6483, Feb. 19, 2020, pp. 1260-1263.
Wu H et al., Development of motavizumab, an ultra-potent antibody for the prevention of respiratory syncytial virus infection in the upper and lower respiratory tract. J Mol Biol. May 4, 2007;368(3):652-65. doi: 10.1016/j.jmb.2007.02.024. Epub Feb. 2, 20070. PMID: 17362988.
Wu, Y. et al., "A noncompeting pair of human neutralizing antibodies block COVID-19 virus binding to its receptor ACE2," Science, vol. 368; 1274-1278 (2020).
Xu, J. et al., "Nanobodies from camelid mice and llamas neutralize SARS-CoV-2 variants," Nature, vol. 595; 278-282 (2021).
Yamin R et al., Fc-engineered antibody therapeutics with improved anti-SARS-CoV-2 efficacy. Nature. Nov. 2021;599(7885): 465-470. doi: 10.1038/s41586-021-04017-w. Epub Sep. 21, 2021. PMID: 34547765; PMCID: PMC9038156.
Yang, D. et al., "Comparison of biosensor platforms in the evaluation of high affinity antibody-antigen binding kinetics," Analytical Biochemistry, vol. 508; 78-96 (2016).
Yonesi, M. and Rezazadeh, A., "Plants as a prospective source of natural anti-viral compounds and oral vaccines against COVID-19 coronavirus," preprint, https://doi.org/10.20944/preprints202004.0321.v1; 31 pages (2020).
Yoshinaga et al., "Ig L-chain Shuffling for Affinity Maturation of Phage Library-derived Human Anti-human MCP-1 Antibody Blocking its Chemotactic Activity" J. Biochem; 143:593-601 (2008).
Young, S. and Linville-Engler, G., "INVIVYD Submits Request for Emergency Use Authorization (EUA) to U.S. FDA for VYD222FOR the Pre-Exposure Prevention of COVID-19 in Immunocompromised Adults Andadolescents," Retrieved from Internet URL: https://investors.adagiotx.com/news-releases/news-release-details/invivyd . . .; 3 pages; Retrieved on Jan. 3, 2024.
Yuan M. et al., A broad and potent neutralization epitope in SARS-related coronaviruses. Proc Natl Acad Sci U S A. Jul. 1, 20229;119(29):e2205784119. doi: 10.1073/pnas.2205784119. Epub Jun. 29, 2022. PMID: 35767670; PMCID: PMC9304036.
Yuan, M. et al., "A higly conserved cryptic epitope in the receptor binding domains of SARS-CoV-2 and SARS-CoV," Science, vol. 368; 4 pages (2020).
Zalevsky, J. et al., "Enhanced antibody half-life improves in vivo activity," Nat. Biotechnol., vol. 28; No. 2; 157-159 (2010).
Zhang A et al., Beyond neutralization: Fc-dependent antibody effector functions in SARS-CoV-2 infection. Nat Rev Immunol. Jun. 2023;23(6):381-396. doi: 10.1038/s41577-022-00813-1. Epub Dec. 19, 2022. PMID: 36536068; PMCID: PMC9761659.
Zhang, F. et al., "Human anti-ACE2 monoclonal antibodies as pan-sarbecovirus prophylactic agents," bioRxiv; https://doi.org/10.1101/2022.08.24.505169; 47 pages (2022).
Zhang, H. et al., "Algorithm for Optimized mRNA Design Improves Stability and Immunogenicity," Nature, https://doi.org/10.1038/s41586-023-06127-z, 52 pages (2023).
Zhao, E. et al., "The Secretogranin II-Derived Peptide Secretoneurin Stimulates Luteinizing Hormone Secretion from Gonadotrophs," Endocrinology, vol. 150; No. 5; 2273-2282 (2009).
Zhao, F. et al., "Broadening a SARS-CoV-1 neutralizing antibody for potent SARS-CoV-2 neutralization through directed evolution," Retrieved from Internet URL: http://biorxiv.org/content/10.1101.2021.05.29.443900v1.full.pdf; 46 ages; Retrieved on Oct. 5, 2021.
Zhou et al. "A general-purpose protein design framework based on mining sequence—structure relationships in known protein structures", Proc Natl Acad Sci U S A. 117(2):1059-68 (2020).
Zhou, D. et al., "Evidence of escape of SARS-CoV-2 variant B.1.351 from natural and vaccine-induced sera," Cell, vol. 184(9); 2348-2361 (2021).
Zhou, P., et al., "A human antibody reveals a conserved site on beta-coronavirus spike proteins and confers protection against SARS-COV-2 infection", Science Translational Medicine, vol. 14, No. 637, Mar. 23, 2022, 2 pages.
Zhou, Q., "Considerations Regarding Assessment of A Modified Monoclonal Antibody (mAb) Product Related to A Prototype mAb Product in Addressing Emerging SARS-CoV-2 Variants—A CMC Perspective," Presentation; EMA-FDA Workshop; Dec. 15, 2022.
Zost SJ et al., Potently neutralizing and protective human antibodies against SARS-CoV-2. Nature. Aug. 2020;584(7821):443-449. doi: 10.1038/s41586-020-2548-6. Epub Jul. 15, 2020. PMID: 32668443; PMCID: PMC7584396.
Abbasi J., "Researchers Tie Severe Immunosuppression to Chronic COVID-19 and Virus Variants," JAMA, vol. 325; No. 20; 2033-2035 (2021).
Agrawal U et al., Severe COVID-19 outcomes after full vaccination of primary schedule and initial boosters: pooled analysis of national prospective cohort studies of 30 million individuals in England, Northern Ireland, Scotland, and Wales. Lancet. Oct. 15, 2022;400(10360):1305-1320. doi: 10.1016/S0140-6736(22)01656-7. PMID: 36244382; PMCID: PMC9560746.
Almagro et al., "Progress and Challenges in the Design and Clinical Development of Antibodies for Cancer Therapy" Front. Immunol., 8:1751, doi: 10.3389/fimmu.2017.01751 (2018).
Andreano, E. et al., "mRNA vaccines and hybrid immunity use different B cell germlines to neutralize Omicron BA.4 and BA.5," bioRxiv, https://doi.org/10.1101/2022.08.04.502828; 31 pages (2022).
Aschner, C.B. et al., "A multi-specific, multi-affinity antibody platform neutralizes sarbecoviruses and confers protection against SARS-CoV-2 in vivo," Sci. Transl. Med., vol. 15(697); eadf4549, 13 pages (2023).
Australian Government, "Australian Public Assessment Report for Sotrovimab," Proprietary Product Name: Xevudy, Sponsor: GlaxoSmithKline Australia Pty Ltd; 58 pages (2021).
Barnes CO et al., SARS-CoV-2 neutralizing antibody structures inform therapeutic strategies. Nature. Dec. 2020;588(7839):682-687. doi: 10.1038/s41586-020-2852-1. Epub Oct. 12, 2020. PMID: 33045718; PMCID: PMC8092461.
Bartsch, Y.C. et al., "Antibody effector functions are associated with protection from respiratory syncytial virus," Cell, vol. 185; 4873-4886 (2022).
Bassetti M. et al., Co-localization of secretogranins/chromogranins with thyrotropin and luteinizing hormone in secretory granules of cow anterior pituitary. J Histochem Cytochem. Sep. 1990;38(9):1353-63. doi: 10.1177/38.9.2387987. PMID: 2387987.
Baum A. et al., "REGN-COV2 antibodies prevent and treat SARSCoV-2 infection in rhesus macaques and hamsters," Science, vol. 370; No. 6520; 1110-1115 (2020).
Baum, A. et al., "Antibody cocktail to SARS-CoV-2 spike protein prevents rapid mutational escape seen with individual antibodies," Science, vol. 369; 1014-1018 (2020).
Bender Ignacio RA et al., Comparative Pharmacokinetics of Tixagevimab/Cilgavimab (AZD7442) Administered Intravenously Versus Intramuscularly in Symptomatic SARS-CoV-2 Infection. Clin Pharmacol Ther. Dec. 2022;112(6):1207-1213. doi: 10.1002/cpt.2706. Epub Jul. 26, 2022. PMID: 35797235; PMCID: PMC9349574.
Boggiano, C. et al., "Update on and Future Directions for Use of Anti-SARS-CoV-2 Antibodies: National Institutes of Health Summit on Treatment and Prevention of COVID-19," Ann Intern Med, 9 pages (2021).
Böttcher E et al. Proteolytic activation of influenza viruses by serine proteases TMPRSS2 and HAT from human airway epithelium. J Virol. Oct. 2006;80(19):9896-8. doi: 10.1128/JVI.01118-06. PMID: 16973594; PMCID: PMC1617224.
Bournazos S et al., Broadly neutralizing anti-HIV-1 antibodies require Fc effector functions for in vivo activity. Cell. Sep. 11, 2014;158(6):1243-1253. doi: 10.1016/j.cell.2014.08.023. PMID: 25215485; PMCID: PMC4167398.
Bruel, T., "Evidence in support of the use of serum neutralisation data to justify a dose increase of monoclonal antibodies to tackle

(56) References Cited

OTHER PUBLICATIONS new variants," EMA/FDA joint meeting, Institut Pasteur, Virus and Immunity Unit, Olivier Schwartz's Lab, 15 pages (2022).

Bulun, S.E., "Reproductive Physiology," Physiology and Pathology of the Female Reproductive Axis, Chapter 17; pp. 590-663; Williams Textbook of Endocrinology, Fourteenth Edition (2020).

Burnett, D.L. et al., "Immunizations with diverse sarbecovirus receptor-binding domains elicit SARS-CoV-2 neutralizing antibodies against a conserved site of vulnerability," Immunity, vol. 54(12); 2908-2921 (2021).

Cao Z et al., VV116 versus Nirmatrelvir-Ritonavir for Oral Treatment of Covid-19. N Engl J Med. Feb. 2, 2023;388(5):406-417. doi: 10.1056/NEJMoa2208822. Epub Dec. 28, 2022. PMID: 36577095; PMCID: PMC9812289.

Cao Z et al., VV116 versus Nirmatrelvir-Ritonavir for Oral Treatment of Covid-19. N Engl J Med. Feb. 2, 2023;388(5):406-417. doi: 10.1056/NEJMoa2208822. Epub Dec. 28, 2022. PMID: 36577095; PMCID: PMC9812289; Supplemental Information.

Cao Z et al., VV116 versus Nirmatrelvir-Ritonavir for Oral Treatment of Covid-19. N Engl J Med. Feb. 2, 2023;388(5):406-417. doi: 10.1056/NEJMoa2208822. Epub Dec. 28, 2022. PMID: 36577095; PMCID: PMC9812289; The Protocol.

Cao, Y. et al., "B.1.1.529 escapes the majority of SARS-CoV-2 neutralizing antibodies of diverse epitopes," bioRxiv, 30 pages (2021).

Cao, Y. et al., "BA.2.12.1, BA.4 and BA.5 escape antibodies elicited by Omicron infection," Nature, vol. 608(7923); 593-602 (2022).

Cao, Y. et al., "Imprinted SARS-CoV-2 humoral immunity induces convergent Omicron RBD evolution," bioRxiv, 38 pages (2022).

Cao, Y. et al., "Omicron BA.2 specifically evades broad sarbecovirus neutralizing antibodies," bioRxiv, 39 pages (2022).

Case JB et al., Neutralizing Antibody and Soluble ACE2 Inhibition of a Replication-Competent VSV-SARS-CoV-2 and a Clinical Isolate of SARS-CoV-2. Cell Host Microbe. Sep. 9, 2020;28(3):475-485.e5. doi: 10.1016/j.chom.2020.06.021. Epub Jul. 3, 2020. PMID: 32735849; PMCID: PMC7332453.

Case JB et al., Resilience of S309 and AZD7442 monoclonal antibody treatments against infection by SARS-CoV-2 Omicron lineage strains. Nat Commun. Jul. 2, 2022;13(1):3824. doi: 10.1038/s41467-022-31615-7. PMID: 35780162; PMCID: PMC9250508.

Case, B., "Development of a Pan-Sarbecovirus Mucosal Vaccine," Instructor in Medicine Washington University School of Medicine IDWeek: Next Generation COVID-19 Vaccines, Boston, MA, 16 pages (2023).

Cathcart A.L. et al., "The dual function monoclonal antibodies VIR-7831 and VIR-7832 demonstrate potent in vitro and in vivo activity against SARS-CoV-2," BioRxiv, https://doi.org/10.1101/2021.03.09.434607 (2022).

Center for Drug Evaluation and Research, Approval Package for: Application No. 761108Orig1s000, Trade Name: Ultomiris Injection, 300 mg / 30mL (10 mg / mL), retrieved from Internet URL: https://www.google.com/url?sa=t&rct=j&q=&esrc=s&source=web&cd=&ved=2ahUKEwiy7dHKnIOEAxXcrokEHUWyB-EQFnoECA4QAQ&url=https%3A%2F%2Fwww.accessdata.fda.gov%2Fdrugsatfda_docs%2Fnda%2F2018%2F761108O.

Centers for Disease Control and Prevention website. COVID-19 vaccines for people who are moderately or severely immunocompromised. Updated Jan. 31, 2023. Accessed Feb. 17, 2023. https://www.cdc.gov/coronavirus/2019-ncov/vaccines/recommendations/immuno.html.

Cerutti, G. et al., "Structural basis for accommodation of emerging B.1.351 and B.1.1.7 variants by two potent SARSCoV-2 neutralizing antibodies," Structure, vol. 29(7); 655-663 (2021).

Chan, J.F. et al., "Simulation of the Clinical and Pathological Manifestations of Coronavirus Disease 2019 (COVID-19) in a Golden Syrian Hamster Model: Implications for Disease Pathogenesis and Transmissibility," Clin Infect Dis., vol. 71; No. 9; 2428-2446 (2020).

Chan, K.K. et al., "Engineering human ACE2 to optimize binding to the spike protein of SARS coronavirus 2," Science. Sep. 4, 2020;369(6508):1261-1265. doi: 10.1126/science.abc0870. Epub Aug. 4, 2020. PMID: 32753553; PMCID: PMC7574912.

Chen et al. "CoV-Spectrum: analysis of globally shared SARS-CoV-2 data to identify and characterize new variants", Bioinformatics 38(6):1735-37 (2022).

Chen, J. et al., "Review of COVID-19 Antibody Therapies," Cornell University Library, New York, 30 pages (2020).

Chen, P. et al., "First-in-Human Study of Bamlanivimab in a Randomized Trial of Hospitalized Patients With COVID-19," Clinical Pharmacology & Therapeutics, vol. 110; No. 6; 1467-1477 (2021).

Chigutsa, E. et al., "A Quantitative Modeling and Simulation Framework to Support Candidate and Dose Selection of Anti-SARS-CoV-2 Monoclonal Antibodies to Advance Bamlanivimab Into a First-in-Human Clinical Trial," Clinical Pharmacology & Therapeutics, vol. 111; No. 3; 595-604 (2022).

Chigutsa, E. et al., "Population Pharmacokinetics and Pharmacodynamics of the Neutralizing Antibodies Bamlanivimab and Etesevimab in Patients With Mild to Moderate COVID-19 Infection," Clinical Pharmacology & Therapeutics, vol. 110; No. 5; 1302-1310 (2021).

Choy, R.K.M. et al., "Controlled Human Infection Models To Accelerate Vaccine Development," Clinical Microbiology Reviews, vol. 35; Issue 3; 163 pages (2022).

Copin, R. et al., "The monoclonal antibody combination REGEN-COV protects against SARS-CoV-2 mutational escape in preclinical and human studies," Cell, vol. 184(15); 3949-3961 (2021).

Corbett, K.S. et al., "Immune Correlates of Protection by mRNA-1273 Vaccine against SARS-CoV-2 in Nonhuman Primates," Science, vol. 373; No. 6561; eabj0299; 23 pages (2021).

Correa Giron, C. et al., "On the interactions of the receptor-binding domain of SARS-CoV-1 and SARS-CoV-2 spike proteins with monoclonal antibodies and the receptor ACE2," Virus Research, vol. 285; 198021; 13 pages (2020).

Corti et al. "Tackling COVID-19 with neutralizing monoclonal antibodies", Cell 184(12):3086-3108 (2021).

Crawford JL & McNeilly AS. Co-localisation of gonadotrophins and granins in gonadotrophs at different stages of the oestrous cycle in sheep. J Endocrinol. Aug. 2002; 174(2):179-94. doi: 10.1677/joe.0.1740179. PMID: 12176657.

Crawford KHD et al., Protocol and Reagents for Pseudotyping Lentiviral Particles with SARS-CoV-2 Spike Protein for Neutralization Assays. Viruses. May 6, 2020; 12(5):513. doi: 10.3390/v12050513. PMID: 32384820; PMCID: PMC7291041.

Credle, J.J. et al., "Unbiased discovery of autoantibodies associated with severe COVID-19 via genome-scale self-assembled DNA-barcoded protein libraries," Nature Biomedical Engineering, vol. 6(8); 992-1003 (2022).

Cromer D et al., Neutralising antibody titres as predictors of protection against SARS-CoV-2 variants and the impact of boosting: a meta-analysis. Lancet Microbe. Jan. 2022;3(1):e52-e61. doi: 10.1016/S2666-5247(21)00267-6. Epub Nov. 15, 2021. PMID: 34806056; PMCID: PMC8592563.

Cuccarese, M.F. et al., "Functional immune mapping with deep-learning enabled phenomics applied to immunomodulatory and COVID-19 drug discovery," bioRxiv, 24 pages (2020).

Database, Rcsb Pdb [Online], "7NAB Crystal structure of human neutralizing mAb CV3-25 binding to SARS-CoV-2 SMPER peptide 1140-1165", 5 pages, PDB Doi: https://doi.org/10.2210/pdb7NAB/pdb (2021).

Highlights of Emergency Use Authorization, Evusheld, 27 pages (2021).

Highlights of Emergency Use Authorization, Evusheld; 30 pages; Revised Jan. 2023.

Hirsch C. et al., "SARS-CoV-2-neutralising monoclonal antibodies to prevent COVID-19," Cochrane Database Syst Rev., Issue 6; Art No. CD014945; 106 pages (2022).

Hirsch C. et al., "SARS-CoV-2-neutralising monoclonal antibodies to prevent COVID-19," Cochrane Database Syst Rev., vol. 6; Issue 6; Art No. CD014945; 89 pages (2022).

Holland et al., ACTIV-3—Therapeutics for Inpatients with COVID-19 (TICO) Study Group. Tixagevimab-cilgavimab for treatment of patients hospitalised with COVID-19: a randomised, double-blind, phase 3 trial. Lancet Respir Med. Oct. 2022;10(10):972-984. doi:

(56) References Cited

OTHER PUBLICATIONS 10.1016/S2213-2600(22)00215-6. Epub Jul. 8, 2022. Erratum in: Lancet Respir Med. Nov. 7, 2022;: PMID: 35817072; PMCID: PMC9270059.

Hu, D. and Irving, A. T., "Massively-multiplexed epitope mapping techniques for viral antigen discovery," Front. Immunol., vol. 14; 1192385; 13 pages (2023).

Hua L et al., MEDI4893* Promotes Survival and Extends the Antibiotic Treatment Window in a *Staphylococcus aureus* Immunocompromised Pneumonia Model. Antimicrob Agents Chemother. Aug. 2015;59(8):4526-32. doi: 10.1128/AAC.00510-15. Epub May 18, 2015. PMID: 25987629; PMCID: PMC4505239.

Huang, Y. et al., "Identification of a conserved neutralizing epitope present on spike proteins from all highly pathogenic coronaviruses," bioRxiv, 27 (2021).

Huang, Y. et al., "Identification of a conserved neutralizing epitope present on spike proteins from all highly pathogenic coronaviruses," bioRxiv, 27; Supplemental Information (2021).

Hurlburt N.K. et al., "Structural definition of a pan-sarbecovirus neutralizing epitope on the spike S2 subunit," Commun Biol., vol. 5; No. 1; 342; 13 Pages (2022).

Ingraham et al. "Generative models for graph-based protein design", 33rd Conference on Neural Information Processing Systems (Neurl PS 2019), Vancouver, Canada.

Irvin SC et al., REGEN-COV® antibody cocktail bioanalytical strategy: comparison of LC-MRM-MS and immunoassay methods for drug quantification. Bioanalysis. Dec. 2021; 13(24): 1827-1836. doi: 10.4155/bio-2021-0190. Epub Nov. 8, 2021. PMID: 34743612; PMCID: PMC8579949.

Isa F et al., Repeat subcutaneous administration of casirivimab and imdevimab in adults is well-tolerated and prevents the occurrence of COVID-19. Int J Infect Dis. Sep. 2022; 122:585-592. doi: 10.1016/j.ijid.2022.06.045. Epub Jul. 2, 2022. PMID: 35788416; PMCID: PMC9249725.

Ishino, T. et al., "Engineering a Monomeric Fc Domain Modality by N-Glycosylation for the Half-life Extension of Biotherapeutics," Journal of Biological Chemistry, vol. 288; No. 23; 16529-16537 (2013).

Janeway et al., The Recognition of Antigen, Immunobiology, 3rd edition, Garland Publishing Inc., 1997, pp. 3:1-3:11.

Jennewein M.F. et al., "Isolation and characterization of crossneutralizing coronavirus antibodies from COVID-19+ subjects," Cell Rep. vol. 36; No. 2; 109353; 22 Pages (2021).

Jette, C.A. et al., "Broad cross-reactivity across sarbecoviruses exhibited by a subset of COVID-19 donor-derived neutralizing antibodies," Cell Reports, vol. 36; 109760; 23 pages (2021).

Jiang, N. et al., "Bivalent mRNA vaccine improves antibody-mediated neutralization of many SARS-CoV-2 Omnicron lineage variants," bioRxiv; 21 pages (2023).

Jiang, W. et al., "Characterization of MW06, a human monoclonal antibody with cross-neutralization activity against both SARS-CoV-2 and Sars-CoV," MABS, vol. 13; No. 1; e1953683; 12 pages (2021).

Jones, B.E. et al., "The neutralizing antibody, LY-CoV555, protects against SARS-CoV-2 infection in nonhuman primates," Sci. Transl. Med., vol. 13; eabf1906; 17 pages (2021).

JP Morgan Healthcare Conference, Regeneron; Retrieved from Internet URL: https://investor.regeneron.com/events/event-details/41st-annual-jp-morgan-healthcare-conference; 37 pages; Retrieved on Jan. 29, 2024.

Ju, B. et al., "Potent human neutralizing antibodies elicited by SARS-CoV-2 infection," retrieved from Internet URL: http://www.biorxiv.org/content/10.1101/2020.03.21.990770V2.full.pdf; 42 Pages; Retrieved on Oct. 6, 2020.

Kaku Y et al., Virological characteristics of the SARS-CoV-2 JN. 1 variant. Lancet Infect Dis. Feb. 2024;24(2):e82. doi: 10.1016/S1473-3099(23)00813-7. Epub Jan. 3, 2024. PMID: 38184005.

KC, B.B. et al., "A machine learning platform to estimate anti-SARS-CoV-2 activities," Nature Machine Intelligence, https://doi.org/10.1038/s42256-021-00335-w; 9 pages (2021).

Khoury DS et al., Neutralizing antibody levels are highly predictive of immune protection from symptomatic SARS-CoV-2 infection. Nat Med. Jul. 2021;27(7):1205-1211. doi: 10.1038/s41591-021-01377-8. Epub May 17, 2021. PMID: 34002089.

Killingley, B. et al., "Safety, tolerability and viral kinetics during SARS-CoV-2 human challenge in young adults," Nature Medicine, vol. 28, 1031-1041 (2022).

Knierman, M.D. et al., "The Human Leukocyte Antigen Class II Immunopeptidome of the SARS-CoV-2 Spike Glycoprotein," Cell Reports, vol. 33; 1 08454; 15 pages (2020).

Kreuzberger N. et al., "SARS-CoV-2-neutralising monoclonal antibodies for treatment of COVID-19," Cochrane Database Syst Rev, vol. 9; No. 9 229 pages (2021).

Kupferschmidt, K., "Evolving threat," Science, vol. 373; No. 6557; 844-849 (2021).

Kurasaki, H. et al., "Safety and Pharmacokinetics of PA-001, a New Potential COVID-19 Drug That Targets the S2 Subunit of SARS-CoV-2 Spike Protein, in Healthy Subjects," Poster Abstracts; Abstract citation ID: ofad500.2142 (2023).

Kurhade C et al., Low neutralization of SARS-CoV-2 Omicron BA.2.75.2, BQ. 1.1 and XBB. 1 by parental mRNA vaccine or a BA.5 bivalent booster. Nat Med. Feb. 2023;29(2):344-347. Safety and efficacy of inhaled IBIO123 for severe covid (preprint).

Ladde, S.M. et al., "Safety and efficacy of inhaled IBIO123 for severe COVID-19: a randomised, double-blind, dose-ascending, placebo-controlled, phase 1/2 trial," The Lancet, 35 pages (2023).

Ladner et al. "Epitope-resolved profiling of the SARS-CoV-2 antibody response identifies cross-reactivity with endemic human coronaviruses", Jan. 1, 2021 (Jan. 1, 2021), vol. 2, No. 1, p. 100189, Retrieved from the Internet: URL: https://www.cell.com/cell-reports-medicine/pdfExtended/S2666-3791(20)30244-5 XP055847640, DOI: 10.1016/j.xcrm.2020.100189, ISSN:2666-3791.

Laracy JC et al., Long and persistent COVID-19 in patients with hematologic malignancies: from bench to bedside. Curr Opin Infect Dis. Aug. 1, 2022;35(4):271-279. doi: 10.1097/QCO.0000000000000841. Epub Jul. 5, 2022. PMID: 35849516; PMCID: PMC9922441.

Leach, M.W. et al., "Use of tissue cross-reactivity studies in the development of antibody-based biopharmaceuticals: history, experience, methodology, and future directions," Toxicol Pathol, vol. 38; No. 7; 1138-1166 (2010).

Levin EG et al., Waning Immune Humoral Response to BNT162b2 Covid-19 Vaccine over 6 Months. N Engl J Med. Dec. 9, 2021;385(24):e84. doi: 10.1056/NEJMoa2114583. Epub Oct. 6, 2021. PMID: 34614326; PMCID: PMC8522797.

Levin M.J. et al., "Intramuscular AZD7442 (Tixagevimab-Cilgavimab) for Prevention of Covid-19," N. Engl. J. Med., vol. 386; No. 23; 2188-2200 (2022).

Levin M.J. et al., "Intramuscular AZD7442 (Tixagevimab-Cilgavimab) for Prevention of Covid-19," N. Engl. J. Med., vol. 386; No. 23; 2188-2200; The Protocol; 424 pages (2022).

Levin, M.J. et al., "AZD7442 (Tixagevimab/Cilgavimab) for Post-Exposure Prophylaxis of Symptomatic Coronavirus Disease 2019," Clinical Infectious Diseases, vol. 76; No. 7; 1247-1256 (2023).

Li W. et al., "Structural basis and mode of action for two broadly neutralizing antibodies against SARS-CoV-2 emerging variants of concern," Cell Rep., vol. 38; No. 2; 110210; 28 pages (2022).

Li, T. et al., "A synthetic nanobody targeting RBD protects hamsters from SARS-CoV-2 infection," Nature Communication, vol. 12; 4635; 13 pages (2021).

Liu Z et al., Identification of SARS-CoV-2 spike mutations that attenuate monoclonal and serum antibody neutralization. Cell Host Microbe. Mar. 10, 2021;29(3):477-488.e4. doi: 10.1016/j.chom.2021.01.014. Epub Jan. 27, 2021. PMID: 33535027; PMCID: PMC7839837.

Liu, H. and Wilson, I.A., "Protective neutralizing epitopes in SARS-CoV-2," Immunol Rev, vol. 310; No. 1; 76-92 (2022).

Liu, H et al., "A combination of cross-neutralizing antibodies synergizes to prevent SARS-CoV-2 and SARS-CoV pseudovirus infection," Cell Host & Microbe, vol. 29; 806-818 (2021).

Liu, L. et al., "Anti—spike IgG causes severe acute lung injury by skewing macrophage responses during acute SARS-CoV infection," JCI Insight, vol. 4; No. 4; e123158; 20 pages (2019).

(56) References Cited

OTHER PUBLICATIONS

Liu, L. et al., "Antibodies targeting a quaternary site on SARS-CoV-2 spike glycoprotein prevent viral receptor engagement by conformational locking," Immunity, vol. 56(10); 2442-2455 (2023).
Liu, L. et al., "Potent neutralizing antibodies against multiple epitopes on SARS-CoV-2 spike," Nature, vol. 584; 450-456 (2020).
Loo, Y.M. et al., "The SARS-CoV-2 monoclonal antibody combination, AZD7442, is protective in nonhuman primates and has an extended half-life in humans," Sci. Transl. Med., vol. 14; No. 635; eabl8124; 15 Pages (2022).
Low, J.S et al., "ACE2 engagement exposes the fusion peptide to pan-coronavirus neutralizing antibodies," bioRxiv, 56 pages (2022).
Magar, R. et al., "Potential Neutralizing Antibodies Discovered for Novel Corona Virus Using Machine Learning," Cornell University Library, New York, 35 pages (2020).
Service, R.F., "New antibodies that the coronavirus can't elude," Science, vol. 380; Issue 6647; 779-780 (2023).
Seydoux E et al., Analysis of a SARS-CoV-2-Infected Individual Reveals Development of Potent Neutralizing Antibodies with Limited Somatic Mutation. Immunity. Jul. 14, 2020;53(1):98-105.e5. doi: 10.1016/j.immuni.2020.06.001. Epub Jun. 8, 2020. PMID: 32561270; PMCID: PMC7276322.
Sheridan, D. et al., "Design and preclinical characterization of ALXN1210: A novel anti-C5 antibody with extneded duration of action," PLos One, vol. 13; No. 4; e0195909; 15 pages (2018).
Sherman, A.C. et al., "The Future of Flu: A Review of the Human Challenge Model and Systems Biology fort Advancement of Influenza Vaccinology," Frontiers in Cellular and Infection Microbiology, vol. 9; Article 107; 9 pages (2019).
Sheward, D.J. et al., "Structural basis of Omicron neutralization by affinity-matured public antibodies," bioRxiv, 24 pages (2022).
Shi, R. et al., "A human neutralizing antibody targets the receptor-binding site of SARS-CoV-2," Nature, vol. 584; No. 7819; 120-124 (2020).
Sia SF, Yan LM, Chin AWH, et al. Pathogenesis and transmission of SARS-CoV-2 in golden hamsters. Nature. 2020;583(7818):834-838.
Sia, S.F. et al., "Pathogenesis and transmission of SARS-CoV-2 in golden hamsters," Nature, vol. 583; 834-837; Supp'l Data included (2020).
Snijder J et al., An Antibody Targeting the Fusion Machinery Neutralizes Dual-Tropic Infection and Defines a Site of Vulnerability on Epstein-Barr Virus. Immunity. Apr. 17, 2018;48(4):799-811. e9. doi: 10.1016/j.immuni.2018.03.026. PMID: 29669253; PMCID: PMC5909843.
Song et al. "Cytokine storm induced by SARS-CoV-2", Clin Chim Acta. 509:280-7 (2020).
Song, Y. et al., "Effects of Secretoneurin and Gonadotropin-Releasing Hormone Agonist on the Spawning of Captive Greater Amberjack (Seriola dumerili)," Life, vol. 12; 1457; 14 pages (2022).
Stadler, E. et al., "Determinants of passive antibody effectiveness in SARS-CoV-2 infection," medRxiv; https://doi.org/10.1101/2022.03.21.22272672; 28 pages (2022).
Stadler, E. et al., "Monoclonal antibody levels and protection from COVID-19," medRxiv; https://doi.org/10.1101/2022.11.22.22282199; 26 pages (2022).
Stamatatos L et al., mRNA vaccination boosts cross-variant neutralizing antibodies elicited by SARS-CoV-2 infection. Science. Mar. 25, 2021;372(6549): 1413-8. doi: 10.1126/science.abg9175. Epub ahead of print. PMID: 33766944; PMCID: PMC8139425.
Starr, T.N. et al., "SARS-CoV-2 Rbd antibodies that maximize breadth and resistance to escape," Nature, https://doi.org/10.1038/s41586-021-03807-6; 36 pages (2021).
Stryer, L., Biochemistry, 4th edition, W. H. Freeman and Company, 1995, pp. 18-23.
Sun, B., "Neutralization mechanism of a human antibody with pan-coronavirus reactivity including SARS-CoV-2," Nature Portfolio, Nature Microbiology, Reviewer comments & Editors Decisions, 55 pages, No. Date Given.
Sun, D. et al., "Potent neutralizing nanobodies resist convergent circulating variants of SARS-CoV-2 by targeting diverse and conserved epitopes," Nature Communications, vol. 12; 4676; 14 pages (2021).
Sun, X. et al., "Neutralization mechanism of a human antibody with pan-coronavirus reactivity including SARS-CoV-2," Nature Microbiology, vol. 7; 1063-1074 (2022).
Sun, X. et al., "Neutralization mechanism of a human antibody with pan-coronavirus reactivity including SARS-CoV-2," Nature Microbiology, vol. 7; 1063-1074; Supplemental Data (2022).
Tabynov, K. et al., "An adjuvanted subunit SARS-CoV-2 spike protein vaccine provides protection against Covid-19 infection and transmission," npj Vaccines, vol. 7; No. 24; 10 pages (2022).
Tao, K. et al., "The biological and clinical significance of emerging Sars-CoV-2 variants," Nature Reviews Genet., vol. 22; 757-773 (2021).
Ter Meulen J et al., Human monoclonal antibody as prophylaxis for SARS coronavirus infection in ferrets. Lancet. Jun. 26, 2004;363(9427):2139-41. doi: 10.1016/S0140-6736(04)16506-9. PMID: 15220038; PMCID: PMC7112500.
Ter Meulen, J. et al., "Human Monoclonal Antibody Combination against SARA Coronavirus: Synergy and Coverage of Escape Mutants," PloS; vol. 3; Issue 7; e237; 9 pages (2006).
Tian, X. et al., "Potent binding of 2019 novel coronavirus spike protein by a SARA coronavirus-specific human monoclonal antibody," Emerging Microbes & Infections, vol. 9; 4 pages (2020).
Tortorici et al. "Broad sarbecovirus neutralization by a human monoclonal antibody", Nature. Sep. 2021;597 (7874): 103-108. doi: 10.1038/s41586-021-03817-4. Epub Jul. 19, 20219 PMID: 34280951.
Tortorici et al. "Broad sarbecovirus neutralization by a human monoclonal antibody", Nature. Sep. 2021;597 (7874): 103-108. doi: 10.1038/s41586-021-03817-4. Epub Jul. 1, 20219 PMID: 34280951; Suppl. info.
Tortorici, M.A. et al., "Ultrapotent human antibodies protect against SARS-CoV-2 challenge via multiple mechanisms," Science, vol. 370; 950-957 (2020).
Trudeau VL et al., Is secretoneurin a new hormone? Gen Comp Endocrinol. Jan. 1, 2012;175(1): 10-8. doi: 10.1016/j.ygcen.2011.10.008. Epub Oct. 20, 2011. PMID: 22036841.
Turelli, P. et al., "P2G3 human monoclonal antibody neutralizes SARS-CoV-2 Omicron subvariants including BA.4 and BA.5 and Bebtelovimab escape mutants," bioRxiv, 15 pages (2022).
U.S. Department of Health and Human Services, "COVID-19: Developing Drugs and Biological Products for Treatment or Prevention Guidance for Industry," Center for Drug Evaluation and Research (CDER); Center for Biologics Evaluation and Research (CBER); 22 pages (2023).
U.S. Department of Health and Human Services, "Development of Monoclonal Antibody Products Targeting SARS-CoV-2 for Emergency Use Authorization Guidance for Industry," Center for Drug Evaluation and Research (CDER); 14 pages (2023).
Ullah, I. et al., "Live imaging of SARS-CoV-2 infection in mice reveals that neutralizing antibodies require Fc function for optimal efficacy," Immunity, vol. 54; 2143-2158 (2021).
Ullah, I. et al., "Live imaging of SARS-CoV-2 infection in mice reveals that neutralizing antibodies require Fc function for optimal efficacy," Immunity, vol. 54; 2143-2158; Supplemental Information (2021).
Van Egerens, D et al., "Risk of evolutionary escape from neutralizing antibodies targeting SARS-CoV-2 spike protein," medRxiv, https://doi.org/10.1101/2020.11.17.20233726; 28 pages (2020).
Veesler, D. et al., "SARS-CoV-2 S glycoprotein in complex with S2X259 Fab," Worldwide Protein Data Bank, Full wwPDB EM Validation Report; EMDB ID: EMD-24347, PDB ID: 7RA8; 76 pages (2022).
Verstraete, K. et al., "Structure and antagonism of the receptor complex mediated by human TSLP in allergy and asthma," Nature Communications, vol. 8; 14937; 17 pages (2017).
Vir Biotechnology, "Vir Biotechnology Announces Topline Data from Phase 2 PENINSULA Trial Evaluating VIR-2482 for thePrevention of Seasonal Influenza A Illness," Retrieved from Internet URLhttps://investors.vir.bio/news/news-details/2023/Vir-Biotechnology-Announces-Topline-Data . . . ; 3 pages; Retrieved on Dec. 5, 2023.

(56) References Cited

OTHER PUBLICATIONS

Walker KW et al., Pharmacokinetic comparison of a diverse panel of non-targeting human antibodies as matched IgG1 and IgG2 isotypes in rodents and non-human primates. PLoS One. May 23, 2019;14(5): e0217061. doi: 10.1371/journal.pone.0217061. PMID: 31120944; PMCID: PMC6533040.

Walker, L.M. and Burton, D.R., "Passive immunotherapy of viral infections: 'super-antibodies' enter the fray," Nature Reviews, vol. 18; 297-308 (2018).

Walser, M. et al., Highly potent anti-SARS-CoV-2 multi-DARPin therapeutic candidates, bioRxiv, 39 pages (2020).

Wang, C. et al., "A human monoclonal antibody blocking SARS-CoV-2 infection," bioRxiv, 24 pages (2020).

Wang, C. et al., "A human monoclonal antibody blocking SARS-CoV-2 infection," Nature Communications, vol. 11; 2251; 6 pages (2020).

Wang, E.Y. et al., "Diverse functional autoantibodies in patients with COVID-19," Nature, Jul. 2021;595(7866):283-288. doi: 10.1038/s41586-021-03631-y. Epub May 19, 2021. PMID: 34010947.

Wang, N. et al., "Subunit Vaccines Against Emerging Pathogenic Human Coronaviruses," Frontiers in Microbiology, vol. 11; Article 298, 19 pages (2020).

Wang, Q. et al., Alarming antibody evasion properties of rising SARS-COV-2 BQ and XBB subvariants Cell, vol. 186; 279-286 (2023).

Wang, Z. et al., "Analysis of memory B cells identifies conserved neutralizing epitopes on the N-terminal domain of variant SARS-Cov-2 spike proteins," Immunity, vol. 55; 1-15, 24 pages (2022).

Wang, Z. et al., "Analysis of memory B cells identifies conserved neutralizing epitopes on the N-terminal domain of variant SARS-Cov-2 spike proteins," Immunity, vol. 55; 1-15, 24 pages; Supplemental Information (2022).

Weinreich DM et al., REGN-COV2, a Neutralizing Antibody Cocktail, in Outpatients with Covid-19, N Engl J Med. 384(3):238-251 (2021).

Westendorf, K. et al., "LY-CoV1404 (bebtelovimab) potently neutralizes SARS-COV-2 variants," Cell Rep., vol. 39; No. 7; 110812; 72 Pages (2022).

\* cited by examiner

NLCPFGEVFNATKFPSVYAWERKKISNCVADYSVLYNSTFFSTFKCYGVSATKLNDLCFSNVYADSFVVKGDDVRQIAPGQTGVIA

DYNYKLPDDFMGCVLAWNTRNIDATSTGNYNYKYRYLRHGKLRPFERDISNVPFSPDGKPCTPPALNCWPLNDYGFYTTTGIGYQ

PYRVVLSFEGSLEVLFQ (SEQ ID NO: 21)

FIG. 1

```
                                        HCDR1                                                    HCDR2
                                        *****                                  *************
                                        *****                                  **************
Reference  QVQLQESGGGLVQAGGSLRLSCAASGRTFSEYAMGWFRQAPGKEREFVATISWSGGSTYYTDSVKGRFTI
AB-1       QVQLQESGGGLVQAGGSLRLSCAASGRTFSEYAMGWFRQAPGKEREFVATISWSGGSTYYTDSVKGRFTI
AB-2       QVQLQESGGGLVQAGGSLRLSCAASGRTFSEYAMGWFRQAPGKEREFVATISYSGGSTYYTDSVKGRFTI HCDR3
                                       *******        
Reference  SRDNAKNTVYLQMNSLKPDDTAVYYCAAAGLGTVVSEWDYDYDYWGQGTQVTVSSGS  (SEQ ID NO: 3)
AB-1       SRDNAKNTVYLQMNSLKPDDTAVYYCAAAGLGVVLSEWDYDYDYWGQGTQVTVSSGS  (SEQ ID NO: 4)
AB-2       SRDNAKNTVYLQMNSLKPDDTAVYYCAAAGLGVHVSEWDYDYDYWGQGTQVTVSSGS  (SEQ ID NO: 5)
                                           1 2 3
```

ANTIGEN BINDING MOLECULES TARGETING SARS-CoV-2

RELATED APPLICATIONS

This application is a Continuation of International Application No. PCT/US2021/047757, filed on Aug. 26, 2021, published in English, which claims the benefit of U.S. Provisional Application No. 63/070,707, filed on Aug. 26, 2020. The entire teachings of the above applications are incorporated herein by reference.

INCORPORATION BY REFERENCE OF MATERIAL IN XML

This application incorporates by reference the Sequence Listing contained in the following eXtensible Markup Language (XML) file being submitted concurrently herewith:
  a) File name: 57081029002_Sequence_Listing.xml; created May 31, 2023, 28,990 Bytes in size.

BACKGROUND

The SARS-Coronavirus-2 (SARS-CoV-2), a novel coronavirus, first caused a cluster of pneumonia cases (COVID-19) in Wuhan, China. As of Mar. 1, 2020, 79,968 patients in China had tested positive for COVID-19, 2,873 deaths had occurred, equivalent to a mortality rate of 3.6% (95% CI 3.5-3.7) (Baud D. et al., *Lancet Infect Dis.* (2020)). This figure, however, may be an underestimate of the potential threat of COVID-19 in symptomatic patients (Id.).

COVID-19 has been spreading rapidly throughout the world, resulting in a pandemic. The Coronavirus disease (COVID-2019) situation report released from the World Health Organization on Apr. 21, 2020 reported 2,397,216 confirmed infections and 162,956 deaths. Among them, 83,006 new cases and 5,109 deaths were added within the previous 24 hours. Quarantine, isolation, and infection-control measures have been relied on to prevent disease spread, and supportive care for those who become ill (Baden and Rubin, *N Engl J Med.*, (2020)).

SUMMARY

There is a critical need to develop specific antiviral therapeutic agents for preventing transmission of COVID-19 as well as treating COVID-19 patients.

The invention disclosed herein is based, in part, on the discovery that polypeptides of the present invention specifically bind to the Spike glycoprotein of severe acute respiratory syndrome coronavirus 2 (SARS-CoV-2-Spike). Accordingly, the invention generally relates to compositions (e.g., polypeptides, pharmaceutical compositions) and methods that are useful for reducing Spike (e.g., SARS-CoV-2-Spike) mediated viral entry into a cell.

Provided herein are polypeptides that specifically bind SARS-CoV-2-Spike. In one aspect, the invention provides polypeptides that specifically bind SARS-CoV-2-Spike, wherein the polypeptide comprises a paratope that is identical to the paratope of an antibody comprising an amino acid sequence selected from:
  a) SEQ ID NO: 4; or
  b) SEQ ID NO: 5.

In some embodiments, the polypeptide comprises an immunoglobulin heavy chain variable domain ($V_H$).

In another aspect, the invention provides a polypeptide that specifically binds SARS-CoV-2-Spike, wherein the polypeptide comprises an immunoglobulin heavy chain variable domain ($V_H$) amino acid sequence comprising a heavy chain complementarity determining region 1 (HCDR1), a heavy chain complementarity determining region 2 (HCDR2) and a heavy chain complementarity determining region 3 (HCDR3) that are identical to the HCDR1, HCDR2 and HCDR3, respectively, of the amino acid sequence of SEQ ID NO: 4 or SEQ ID NO: 5.

In some embodiments, the polypeptide further comprises a paratope that is identical to the paratope of a single domain antibody comprising:
  a) SEQ ID NO: 4; or
  b) SEQ ID NO: 5.

In another aspect, the invention provides a polypeptide that comprises a $V_H$ comprising the amino acid sequence of SEQ ID NO: 2, wherein:
  a) $X_1$ is not T;
  b) $X_2$ is not V; or
  c) $X_3$ is not V,
or any combination of the foregoing.

In some embodiments, the polypeptide is a single-domain antibody or an antigen-binding fragment thereof.

In some embodiments, the polypeptide is linked to a second polypeptide. The term "linked" means attached, via a covalent or noncovalent interaction. Conjugation can employ a suitable linking agent. Non-limiting examples include peptide linkers, compound linkers, and chemical cross-linking agents. In certain embodiments, the linker is a disulfide bond.

In some embodiments, the polypeptides of the invention are fusion proteins.

In other aspects, the invention provides a polynucleotide encoding a polypeptide disclosed herein, a vector comprising such polynucleotide, and a host cell comprising such polynucleotide or vector.

In another aspect, the invention provides a method of treating a subject in need thereof (e.g., a subject having a SARS-CoV infection, such as COVID-19), comprising administering to the subject an effective amount of a polypeptide disclosed herein or a composition (e.g., pharmaceutical composition) comprising a polypeptide disclosed herein.

In another aspect, the invention provides a method of inhibiting fusion between SARS-CoV-2-Spike and a cell (e.g., a cell in a subject), comprising contacting the cell with an effective amount of a composition comprising a polypeptide disclosed herein or a composition (e.g., pharmaceutical composition) comprising a polypeptide disclosed herein.

BRIEF DESCRIPTION OF THE DRAWINGS

FIG. 1 depicts the amino acid sequence of the receptor binding domain (RBD of SARS-Cov-1-Spike (SEQ ID NO: 21). The epitope residues bound by the Reference antibody disclosed herein are indicated by asterisks.

FIG. 2 depicts an alignment of non-limiting examples of heavy chain variable (VII) sequences that are useful in polypeptides of the invention. The heavy chain complementarity determining region (HCDR) sequences are indicated using bold letters and underlining. Paratope residues are indicated with "*." Additional possible paratope residues— are indicated with "*. ." The position of $X_n$, where n is a number from 1-3, is indicated by the corresponding numbers at the bottom of the alignment. Also see $V_H$ consensus (SEQ ID NO: 2) in Table 1. The antibody sequences were computationally generated using information from the sequence and structure of a reference polypeptide (Reference). Paratope positions were defined as antibody residues within 5 angstroms of the antigen in the parent structures.

FIG. 4 illustrates the ability of a polypeptide of the invention (AB-1) to neutralize mutant SARS-COV-2 pseudovirus. The bars represent fold-difference (WT-Mutant)/(WT) in $IC_{50}$ values for antibody neutralization of pseudoviruses bearing emerging mutations or deletions relative to the parent D614G-parent virus. Values between −2.5 and 2.5 are considered as not significant in this assay.

DETAILED DESCRIPTION

Figure 3:
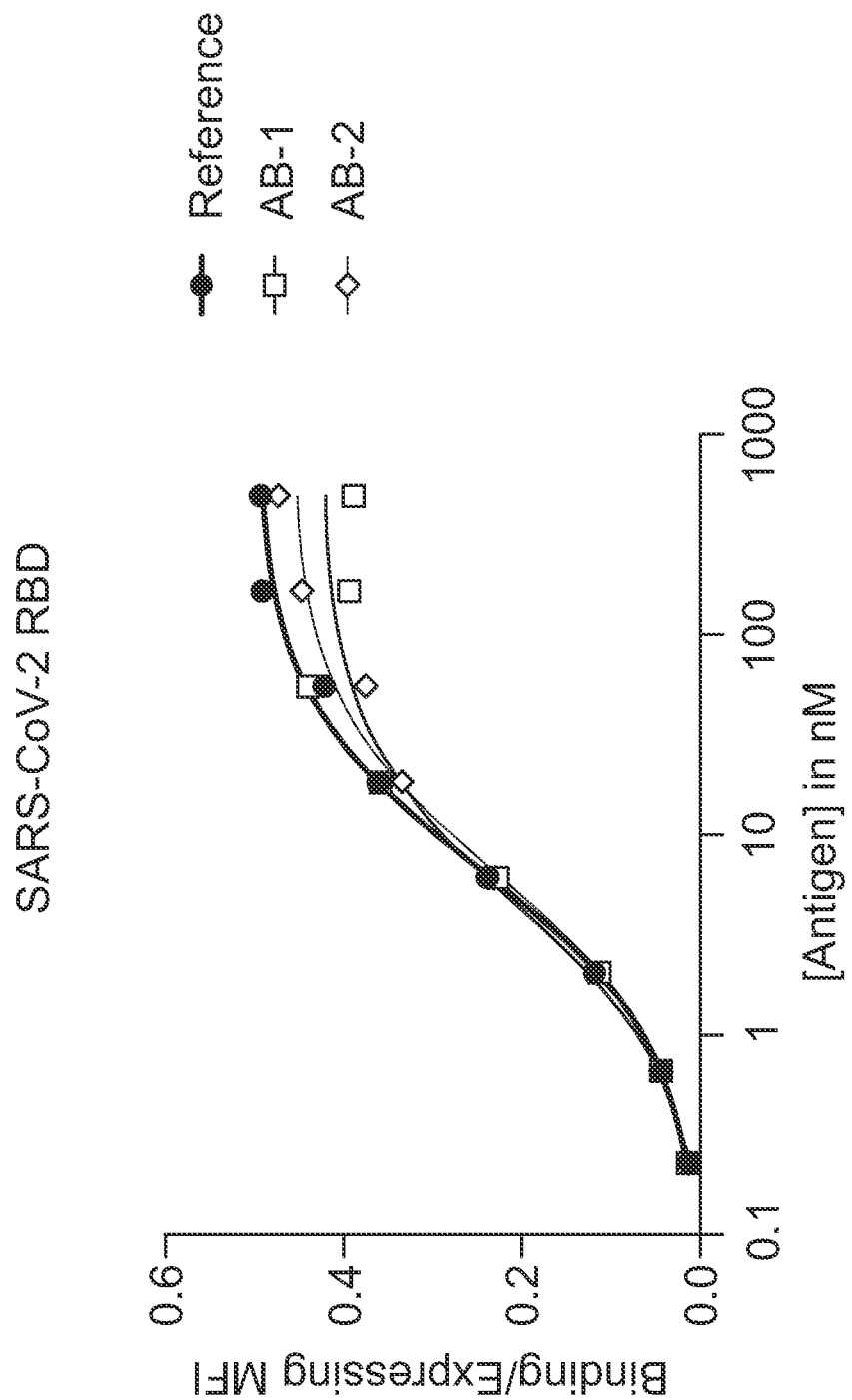
FIG. 3 depicts the affinities of a reference VHH molecule (Reference), and two variant VHH molecules of the invention, AB-1 and AB-2, to COV-2 RBD, as measured using yeast surface display.

A description of example embodiments follows.

Several aspects of the invention are described below, with reference to examples for illustrative purposes only. It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The invention is not limited by the illustrated ordering of acts or events, as some acts may occur in different orders and/or concurrently with other acts or events. Furthermore, not all illustrated acts, steps or events are required to implement a methodology in accordance with the invention. Many of the techniques and procedures described, or referenced herein, are well understood and commonly employed using conventional methodology by those skilled in the art.

Polypeptides Binding SARS-CoV-2 Spike Protein

SARS-CoV-2 is the causative agent of COVID-19. SARS-CoV-2-Spike, or S protein of the SARS-CoV-2, a protein that facilitates entry of the SARS-CoV-2 virus into a host cell, such as a human host cell. Without being bound by theory, it is believed SARS-CoV-2-Spike facilitates infection by binding to an entry receptor on the surface of a host cell (e.g., angiotensin converting enzyme 2 (ACE2) or Transmembrane protease, serine 2 (TMPRSS2)). A non-limiting example of a wildtype SARS-CoV-2-Spike sequence is NCBI RefSeq YP_009724390 (SEQ ID NO: 1).

```
                                             (SEQ ID NO: 1)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG
```

-continued

```
VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPVVNIQKEIDRLNEVAKNLNESLIDLQELGKYEQYIKWP

WYIWLGFIAGLIAIVMVTIMLCCMTSCCSCLKGCCSCGSCCKFDEDDSEP

VLKGVKLHYT.
```

As used herein, SARS-CoV-2 Spike includes wild-type SARS-CoV-2 Spike proteins (e.g., SEQ ID NO: 1), variants of wild-type SARS-CoV-2 Spike proteins, and modified forms of wild-type and variant SARS-CoV-2 Spike proteins.

In one aspect, the invention provides a polypeptide that binds to a SARS-CoV-2 Spike protein comprising SEQ ID NO:1.

In some embodiments, the polypeptide binds to a variant of SARS-CoV-2-Spike. In some embodiments, the variant comprises an amino acid sequence that has at least about 90% sequence identity to the wildtype SARS-CoV-2-Spike sequence (e.g., SEQ ID NO: 1), for example, having at least about: 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence identity to the wildtype SARS-CoV-2-Spike sequence. In some embodiments, the sequence identity is about: 90-99.9%, 90-99.8%, 92-99.8%, 92-99.6%, 94-99.6%, 94-99.5%, 95-99.5%, 95-99.4%, 96-99.4%, 96-99.2%, 97-99.2% or 97-99%.

In some embodiments, the variant SARS-CoV-2-Spike comprises, relative to SEQ ID NO:1, one or more mutations selected from: L5F, S13I, T19R, A67V, 69del, 70del, D80G, T95I, G142D, 144del, W152C, E154K, F157S, A222V, D253G, G261D, V367F, K417N, N439K, L452R, Y453F, S477N, E484K, F486L, S494P, E484Q, N501T, N501Y, F565L, A570D, D614G, Q677H, P681H, P681R, A701V, T716I, T859N, F888L, S982A, D950N, Q957R, Q1071H, V1176F, D1118H, K1191N, or a combination thereof, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or all 45.

In some embodiments, the variant SARS-CoV-2-Spike comprises, relative to SEQ ID NO:1, one or more mutations selected from: 69del, 70del, 144del, E484K, S494P, N501Y, A570D, D614G, P681H, T716I, S982A, DI 18H or K1191N, or a combination thereof. In some embodiments, the variant SARS-CoV-2-Spike comprises 69del, 70del, 144del, N501Y, A570D, D614G, P681H, T716I, S982A, and D1118H. In some embodiments, the variant SARS-CoV-2-Spike further comprises E484K, S494P or K1191N, or a combination thereof.

In some embodiments, the variant SARS-CoV-2-Spike comprises, relative to SEQ ID NO:1, one or more mutations selected from: D80A, D215G, 241del, 242del, 243del, K417N, E484K, N501Y, D614G or A701V, or a combination thereof. In some embodiments, the variant SARS-CoV-2-Spike comprises D80A, D215G, 241del, 242del, 243del, K417N, E484K, N501Y, D614G, and A701V.

In some embodiments, the variant SARS-CoV-2-Spike comprises, relative to SEQ ID NO:1, one or more mutations selected from: T19R, G142D, 156del, 157del, R158G, L452R, T478K, D614G, P681R or D950N, or a combination thereof. In some embodiments, the variant SARS-CoV-2-Spike comprises T19R, 156del, 157del, R158G, L452R, T478K, D614G, P681R, and D950N. In some embodiments, the variant SARS-CoV-2-Spike further comprises G142D.

In some embodiments, the variant SARS-CoV-2-Spike comprises, relative to SEQ ID NO:1, one or more mutations selected from: 69del, 70del, 144del, A222V, G261D, V367F, K417N, N439K, Y453F, S477N, E484K, F486L, N501T, N501Y, A570D or D614G, or a combination thereof.

In some embodiments, the variant SARS-CoV-2-Spike comprises, relative to SEQ ID NO:1, one or more mutations selected from: E484K, N501Y or D614G, or a combination thereof.

In some embodiments, the modified SARS-CoV-2 Spike protein comprises, relative to SEQ ID NO:1, one or more mutations selected from: F817P, A892P, A899P, A942P, K986P, V987P.

In some embodiments, the polypeptide binds the SARS-CoV-2 Spike protein receptor-binding domain (RBD) (SEQ ID NO: 17), or an epitope within RBD (e.g., recognized by RBD Community 7).

(SEQ ID NO: 17)
RVQPTESIVRFPNITNLCPFGEVFNATRFASVYAWNRKRISNCVADYSVL

YNSASFSTFKCYGVSPTKLNDLCFTNVYADSFVIRGDEVRQIAPGQTGKI

ADYNYKLPDDFTGCVIAWNSNNLDSKVGGNYNYLYRLFRKSNLKPFERDI

STEIYQAGSTPCNGVEGFNCYFPLQSYGFQPTNGVGYQPYRVVVLSFELL

HAPATVCGP.

In some embodiments, the polypeptide binds to a variant of the SARS-CoV-2-Spike RBD or an epitope within the SARS-CoV-2-Spike RBD. In some embodiments, the variant comprises an amino acid sequence that has at least about 90% sequence identity to the wildtype SARS-CoV-2-Spike RBD (e.g., SEQ ID NO: 17), for example, having at least about: 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% sequence identity. In some embodiments, the sequence identity is about: 90-99.9%, 90-99.8%, 92-99.8%, 92-99.6%, 94-99.6%, 94-99.5%, 95-99.5%, 95-99.4%, 96-99.4%, 96-99.2%, 97-99.2% or 97-99%.

In some embodiments, the polypeptide that binds to a SARS-CoV-2 Spike protein (e.g., SEQ ID NO: 1, SEQ ID NO: 17) and comprises an immunoglobulin heavy chain variable region, wherein the polypeptide does not comprise all three of SEQ ID NO: 6, SEQ ID NO: 7 and SEQ ID NO: 9. In some embodiments, the polypeptide comprises 1 or 2 CDRs selected from SEQ ID NO: 6, SEQ ID NO: 7 and SEQ ID NO: 9.

In another aspect, the invention provides a polypeptide that specifically binds a SARS-CoV-2 Spike protein, wherein the polypeptide comprises an immunoglobulin heavy chain variable region ($V_H$) comprising an amino acid sequence that is at least 55% (e.g., at least 60, 65, 70, 75, 80, 85, 90, 95, 98, or 99%) identical to SEQ ID NO: 3, wherein the polypeptide does not comprise all three of SEQ ID NO: 6, SEQ ID NO: 7 and SEQ ID NO: 9. In some embodiments, the polypeptide comprises 1 or 2 CDRs selected from SEQ ID NO: 6, SEQ ID NO: 7 and SEQ ID NO: 9.

In some embodiments, the polypeptide binds to a wildtype SARS-CoV-2 Spike protein (e.g., SEQ ID NO:1). In some embodiments, the polypeptide binds to one or more epitope residues of a wildtype SARS-CoV-2 Spike protein (e.g., one or more epitope residues in the SARS-CoV-2 Spike RBD).

As used herein, the term "reference" or "reference polypeptide" refers to a polypeptide (e.g., immunoglobulin molecule) that specifically binds to SARS-CoV-1, and is not a polypeptide of the invention. The sequence of a reference polypeptide and a polypeptide of the invention may be compared to illustrate structural differences between them (e.g., differences at one or more amino acid positions, such as amino acid substitutions). In some embodiments, a polypeptide of the invention will have more than insubstantial differences (e.g., one or more substantial differences) in comparison to a reference polypeptide, such that, generally, polypeptides of the invention will, under controlled conditions, exhibit one or more (i.e., one, two, or all three) of: a different function, in a different way, to achieve a different result, in comparison to a reference polypeptide. Reference polypeptides will vary by one or more amino acids from a polypeptide of the invention, e.g., in some embodiments by 1, 2, 3, 4, 5, 6, 7, 8, 9, 10, 11, 12, 13, 14, 15, 16, 17, 18, 19, 20 or more amino acids. In certain embodiments, a reference polypeptide diverges from a polypeptide provided by the invention by at least about: 0.4, 0.8, 1, 2, 3, 4, 5, 6, 7, 8, 9, 10, 15, 20, 25, 30, 35, 40, 45, 50, 55% or more amino acid identity.

In some embodiments, the "reference polypeptide" is an antibody, referred to herein as "the Reference Antibody," which comprises a $V_H$ region comprising the amino acid sequence of SEQ ID NO: 3. The Reference Antibody is a single-domain camelid antibody that binds SARS-CoV-2 spike RBD and block interaction with ACE2. For additional information about the Reference Antibody, see, e.g., Protein Data Bank (PDB) accession 6WAQ, Huo et al., *Neutralizing nanobodies bind SARS-CoV-2 spike RBD and block interaction with ACE2*, Nat Struct Mol Biol. 27(9):846-54 (2020), and Wrapp et al., *Structural Basis for Potent Neutralization of Betacoronaviruses by Single-Domain Camelid Antibodies*, Cell 181(5):1004-15 (2020)).

As used herein, the term "sequence identity," refers to the extent to which two nucleotide sequences, or two amino acid sequences, have the same residues at the same positions when the sequences are aligned to achieve a maximal level of identity, expressed as a percentage. For sequence alignment and comparison, typically one sequence is designated as a reference sequence, to which a test sequences are compared. The sequence identity between reference and test sequences is expressed as the percentage of positions across the entire length of the reference sequence where the reference and test sequences share the same nucleotide or amino acid upon alignment of the reference and test sequences to achieve a maximal level of identity. As an example, two sequences are considered to have 70% sequence identity when, upon alignment to achieve a maximal level of identity, the test sequence has the same nucleotide or amino acid residue at 70% of the same positions over the entire length of the reference sequence.

Alignment of sequences for comparison to achieve maximal levels of identity can be readily performed by a person of ordinary skill in the art using an appropriate alignment method or algorithm. In some instances, the alignment can include introduced gaps to provide for the maximal level of identity. Examples include the local homology algorithm of Smith & Waterman, *Adv. Appl. Math.* 2:482 (1981), the homology alignment algorithm of Needleman & Wunsch, *J. Mol. Biol.* 48:443 (1970), the search for similarity method of Pearson & Lipman, *Proc. Nat'l. Acad. Sci. USA* 85:2444 (1988), computerized implementations of these algorithms (GAP, BESTFIT, FASTA, and TFASTA in the Wisconsin Genetics Software Package, Genetics Computer Group, 575 Science Dr., Madison, Wis.), and visual inspection (see generally Ausubel et al., *Current Protocols in Molecular Biology*).

When using a sequence comparison algorithm, test and reference sequences are input into a computer, subsequent coordinates are designated, if necessary, and sequence algorithm program parameters are designated. The sequence comparison algorithm then calculates the percent sequence identity for the test sequence(s) relative to the reference sequence, based on the designated program parameters. A commonly used tool for determining percent sequence identity is Protein Basic Local Alignment Search Tool (BLASTP) available through National Center for Biotechnology Information, National Library of Medicine, of the United States National Institutes of Health. (Altschul et al., 1990).

The term "polypeptide" "peptide" or "protein" denotes a polymer of at least two amino acids covalently linked by an amide bond, regardless of length or post-translational modification (e.g., glycosylation or phosphorylation). A protein, peptide or polypeptide can comprise any suitable L- and/or D-amino acid, for example, common α-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and methods for adding or removing protecting groups are known in the art and are described in, for example, Green and Wuts, "*Protecting Groups in Organic Synthesis*," John Wiley and Sons, 1991. The functional groups of a protein, peptide or polypeptide can also be derivatized (e.g., alkylated) or labeled (e.g., with a detectable label, such as a fluorogen or a hapten) using methods known in the art. A protein, peptide or polypeptide can comprise one or more modifications (e.g., amino acid linkers, acylation, acetylation, amidation, methylation, terminal modifiers (e.g., cyclizing modifications), N-methyl-α-amino group substitution), if desired. In addition, a protein, peptide or polypeptide can be an analog of a known and/or naturally-occurring peptide, for example, a peptide analog having conservative amino acid residue substitution(s).

In one aspect, the invention provides a polypeptide that specifically binds SARS-CoV-2-Spike, wherein the polypeptide comprises an immunoglobulin heavy chain variable domain ($V_H$) comprising a paratope that is identical to the paratope of an antibody comprising an amino acid sequence selected from:

a) SEQ ID NO: 4; or
b) SEQ ID NO: 5.

See Table 1 for SEQ ID NOs: 4 and 5 and FIG. 2 for the paratope residues of antibodies comprising SEQ ID NOs: 4 and 5. In some embodiments, the paratope comprises amino acid residues corresponding to S52, W53 or Y53, S54, G56, S57, T58, Y59, G102, T103 or V103, V104 or H104, V105 or L105, S106, E107, W108, Y110 and D111 of SEQ ID NO: 2. In some embodiments, said paratope further comprises amino acid residues corresponding to G55 and D62 of SEQ ID NO: 2.

The term "paratope" refers to a set of amino acid residues in an antibody or an antigen-binding fragment thereof that contribute to a binding interaction with an epitope of a target protein. The binding interaction can be a hydrogen bond, a salt bridge, a van der Waal interaction, an ionic bond or a combination thereof. A binding interaction may be direct, or indirect, e.g., via a coordinated intermediate molecule, such as an ion or water. The residues of a paratope, in some embodiments, comprise only residues that are part of a defined CDR. In other embodiments, the residues of a paratope further comprise one or more residues that are not part of a defined CDR.

In some embodiments, the paratope is oriented less than about 5.0 angstroms from an epitope on a target antigen when the polypeptide is bound to the target antigen, e.g., less than about: 4.5, 4.0, 3.5, 3.0, 2.5, 2.4, 2.3, 2.2, 2.1, 2.0, 1.9, 1.8, 1.7, 1.6, 1.5, 1.4, 1.3, 1.2, 1.1, 1.0 or 0.9 angstroms, or about: 0.9-5.0, 0.9-4.8. 1.0-5, 1.0-4.5, 1.0-4.0, 1.0-3.5, 1.1-3.5, 1.1-3.0, 1.2-3.0, 1.2-2.5, 1.3-2.5, 1.3-2.4, 1.4-2.4, 1.4-2.3, 1.5-2.3, 1.5-2.2, 1.6-2.2, 1.6-2.1, 1.7-2.1, 1.7-2.0 or 1.8-2.0 angstroms, from the epitope. In some embodiments, all of the amino acid residues constituting the paratope are oriented less than about 5.0 angstroms from an epitope on a target antigen when the polypeptide is bound to the target antigen. In other embodiments, less than all of the amino acid residues constituting the paratope (e.g., about 40%, 50%, 60%, 70%, 80%, 90% of the amino acid residues) in the paratope are oriented less than about 5.0 angstroms from an epitope on a target antigen when the polypeptide is bound to the target antigen.

In some embodiments, the polypeptide comprising a paratope disclosed herein further comprises an immunoglobulin light chain variable domain ($V_L$).

In another aspect, the invention provides a polypeptide that specifically binds SARS-CoV-2-Spike, wherein the polypeptide comprises a $V_H$ amino acid sequence comprising a heavy chain complementarity determining region 1 (HCDR1), a heavy chain complementarity determining region 2 (HCDR2) and a heavy chain complementarity determining region 3 (HCDR3) that are identical in amino acid sequence to the HCDR1, HCDR2 and HCDR3, respectively, of SEQ ID NO: 4 or SEQ ID NO: 5.

The CDR (e.g., HCDR1, HCDR2 and/or HCDR3) can be a CDR defined by any art-recognized method for identifying CDR residues of an antibody, as described further herein (e.g., a CDR as defined by Kabat, a CDR as defined by Chothia).

In some embodiments, the polypeptide further comprises a paratope that is identical to the paratope of a single domain antibody comprising the amino acid sequence of:

a) SEQ ID NO: 4; or
b) SEQ ID NO: 5.

In another aspect, the invention provides a polypeptide that specifically binds SARS-CoV-2-Spike, comprising a $V_H$ comprising the amino acid sequence of SEQ ID NO: 2, wherein:

a) $X_1$ is not T;
b) $X_2$ is not V; or
c) $X_3$ is not V, or any combination of the foregoing.

The sequence identified as SEQ ID NO: 2 is shown below, which is a consensus $V_H$ sequence for SEQ ID Nos: 3-5 herein.

(SEQ ID NO: 2)
QVQLQESGGGLVQAGGSLRLSCAASGRTFSEYAMGWFRQAPGKEREFVAT

ISWSGGSTYYTDSVKGRFTISRDNAKNTVYLQMNSLKPDDTAVYYCAAAG

LGX₁X₂X₃SEWDYDYDYWGQGTQVTVSSGS.

In some embodiments:
a) $X_1$ is T or V;
b) $X_2$ is V or H; or
c) $X_3$ is V or L,
or any combination of the foregoing.

In some embodiments:
a) $X_1$ is V;
b) $X_2$ is H; or
c) $X_3$ is L,
or any combination of the foregoing.

In some embodiments, $X_1$ is not T. In some embodiments, $X_1$ is T or V. In some embodiments, $X_1$ is T. In some embodiments, $X_1$ is V. In some embodiments, $X_2$ is not V. In some embodiments, $X_2$ is V or H. In some embodiments, $X_2$ is V. In some embodiments, $X_2$ is H. In some embodiments, $X_3$ is not V. In some embodiments, $X_3$ is V or L. In some embodiments, $X_3$ is V. In some embodiments, $X_3$ is L.

In some embodiments, the polypeptide comprises a $V_H$ that comprises an HCDR1, an HCDR2 and an HCDR3 that are identical in amino acid sequence to the HCDR1, HCDR2 and HCDR3, respectively, of SEQ ID NO: 4 or SEQ ID NO: 5 (see Table 1 for SEQ ID NOs: 4 and 5 and FIG. 2 for corresponding HCDR1, HCDR2 and HCDR3 sequences).

In some embodiments, a polypeptide disclosed herein comprises a $V_H$ that is at least about 70% identical to the amino acid sequence of SEQ ID NO: 3. For example, the $V_H$ can be at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 3. In some embodiments, the $V_H$ is at least about 85% or at least about 90% identical to the amino acid sequence of SEQ ID NO: 3. The sequence identified as SEQ ID NO: 3 is shown below, which corresponds to a human $V_H$ domain:

(SEQ ID NO: 3)
QVQLQESGGGLVQAGGSLRLSCAASGRTFSEYAMGWFRQAPGKEREFVAT

ISWSGGSTYYTDSVKGRFTISRDNAKNTVYLQMNSLKPDDTAVYYCAAAG

LGTVVSEWDYDYDYWGQGTQVTVSSGS

In some embodiments, a polypeptide disclosed herein comprises a $V_H$ that is at least about 70% identical to the amino acid sequence of SEQ ID NO: 4 or SEQ ID NO: 5, or a combination of the foregoing. For example, the $V_H$ can be at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 4 or SEQ ID NO: 5, or a combination of the foregoing. In some embodiments, the $V_H$ is at least about 85% or at least about 90% identical to the amino acid sequence of SEQ ID NO: 4 or SEQ ID NO: 5, or a combination of the foregoing.

In some embodiments, a polypeptide disclosed herein comprises an amino acid sequence that is at least about 70% identical to the amino acid sequence of SEQ ID NO: 15 or SEQ ID NO: 16, or a combination of the foregoing. For example, the amino acid sequence can be at least about: 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 15 or SEQ ID NO: 16, or a combination of the foregoing. In some embodiments, the amino acid sequence is at least about 85% or at least about 90% identical to the amino acid sequence of SEQ ID NO: 15 or SEQ ID NO: 16, or a combination of the foregoing.

In some embodiments, a polypeptide disclosed herein comprises a $V_H$ that comprises at least 1 amino acid substitution relative to the amino acid sequence of SEQ ID NO: 3. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of SEQ ID NO: 3.

In some embodiments, a polypeptide disclosed herein comprises a $V_H$ that comprises at least 1 amino acid substitution relative to the amino acid sequence of SEQ ID NO: 4 or SEQ ID NO: 5, or a combination of the foregoing. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the $V_H$ comprises about 1-10 amino acid substitutions, relative to the amino acid sequence of SEQ ID NO: 4 or SEQ ID NO: 5, or a combination of the foregoing.

In some embodiments, a polypeptide disclosed herein comprises an amino acid sequence that comprises at least 1 amino acid substitution relative to the amino acid sequence of SEQ ID NO: 15 or SEQ ID NO: 16, or a combination of the foregoing. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the amino acid sequence comprises about 1-10 amino acid substitutions, relative to the amino acid sequence of SEQ ID NO: 15 or SEQ ID NO: 16, or a combination of the foregoing.

In some embodiments, the amino acid substitutions are conservative substitutions. The term "conservative amino acid substitution(s)" or "conservative substitution(s)" refers to an amino acid substitution having a value of 0 or greater in BLOSUM62.

In some embodiments, the amino acid substitutions are highly conservative substitutions. The term "highly conservative amino acid substitution(s)" or "highly conservative substitution(s)" refers to an amino acid substitution having a value of at least 1 (e.g., at least 2) in BLOSUM62.

In some embodiments, a polypeptide disclosed herein comprises a $V_H$ that comprises the amino acid sequence of SEQ ID NO: 4 or SEQ ID NO: 5. In some embodiments, a polypeptide disclosed herein comprises a $V_H$ that comprises the amino acid sequence of SEQ ID NO: 4. In some embodiments, a polypeptide disclosed herein comprises a $V_H$ that comprises the amino acid sequence of SEQ ID NO: 5.

In some embodiments, a polypeptide disclosed herein comprises the amino acid sequence of SEQ ID NO: 15 or SEQ ID NO: 16. In some embodiments, a polypeptide disclosed herein comprises the amino acid sequence of SEQ ID NO: 15. In some embodiments, a polypeptide disclosed herein comprises the amino acid sequence of SEQ ID NO: 16.

In some embodiments, a polypeptide disclosed herein comprises a $V_H$ that contains human framework regions.

In some embodiments, a polypeptide disclosed herein is an immunoglobulin molecule, such as an antibody (e.g., a whole antibody, an intact antibody) or an antigen-binding fragment of an antibody. As used herein, the term "antibody" refers to an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" refers to a full-length antibody.

In some embodiments, a polypeptide disclosed herein is a single-domain antibody or an antigen-binding fragment thereof. As used herein, the term "single-domain antibody (sdAb)" or "nanobody" refers to an immunoglobulin molecule consisting of a single monomeric variable antibody domain and capable of specific binding to a target. The single-domain antibody can be of any species, such as a murine antibody, a human antibody or a humanized single-domain antibody.

In some embodiments, a polypeptide disclosed herein is a heavy-chain antibody comprising two or more heavy chains, but lacking light chains, or an antigen-binding fragment thereof. Non-limiting examples of heavy chain antibodies include camelid Vhh (also referred to as VHH or $V_HH$) antibodies. Camelid antibodies are antibodies from the Camelidae family of mammals that include llamas, camels, and alpacas.

In some embodiments, a polypeptide disclosed herein is an antibody comprising two heavy (H) chains and two light (L) chains inter-connected by disulfide bonds or multimers thereof (for example, IgM). Each heavy chain comprises a heavy chain variable region ($V_H$) and a heavy chain constant region (comprising domains CH1, hinge CH2 and CH3). Each light chain comprises a light chain variable region ($V_L$) and a light chain constant region (CL). The $V_H$ and the $V_L$ regions may be further subdivided into regions of hyper-variability, termed complementarity determining regions (CDR), interspersed within framework regions (FR). $V_H$ and $V_L$ each comprises three CDRs and four FR segments, arranged from the amino-terminus to the carboxy-terminus in the following order: FR1, CDR1, FR2, CDR2, FR3, CDR3, and FR4. The antibody can be of any species, such as a murine antibody, a human antibody or a humanized antibody.

The extent of the framework region and the CDRs of an antibody can be identified using one of several suitable methodologies that are well known in the art, for example, by the Kabat definition, the Chothia definition, the AbM definition, and/or the contact definition. Publicly and/or commercially available tools for identifying framework and/or CDR regions include, IgBlast (accessible at www.ncbi.nlm.nih.gov/igblast/), Scaligner (available from drugdesigntech at www.scaligner.com/), IMGT rules and/or tools (see, for example, www.imgt.org/IMGTScientific-Chart/Nomenclature/IMGT-FRCDRdefinition.html, also accessible at www.imgt.org/), Chothia Canonical Assignment (accessible at www.bioinf.org.uk/abs/chothia.html), Antigen receptor Numbering And Receptor CalssificatiIon (ANARCI, accessible at opig.stats.ox.ac.uk/webapps/news-abdab/sabpred/anarci/), or the Paratome web server (accessible at www.ofranlab.org/paratome/, see Vered Kunik, et al, Nucleic Acids Research, Volume 40, Issue W1, 1 Jul. 2012, Pages W521-W524).

As used herein, a "CDR" encompasses any CDR defined by an art-recognized method for identifying the CDR residues on an antibody. See, e.g., Kabat, E. A., et al., (1991) Sequences of Proteins of Immunological Interest, Fifth Edition, U.S. Department of Health and Human Services, NIH Publication No. 91-3242, Chothia et al., (1989) Nature 342:877; Chothia, C. et al., (1987) J. Mol. Biol. 196:901-917; Al-lazikani et al., (1997) J. Molec. Biol. 273:927-948; and Almagro, J. Mol. Recognit. 17:132-143 (2004). See also hgmp.mrc.ac.uk and bioinf.org.uk/abs. Two antibodies are determined to have the same CDR as one another with respect to a HCDR1, HCDR2, HCDR3, LCDR1, LCDR2 and/or LCDR3, when the identity of that CDR is determined for both antibodies using the same method.

In some embodiments, a polypeptide disclosed herein is an antigen-binding fragment of an antibody. The term "antigen-binding fragment" refers to a portion of an immunoglobulin molecule (e.g., a single-domain antibody) that retains the antigen binding properties of the parental full-length single-domain antibody. Non-limiting examples of antigen-binding fragments include a $V_H$ region, a $V_L$ region, an Fab fragment, an F(ab')$_2$ fragment, an Fd fragment, an Fv fragment, and a domain antibody (dAb) consisting of one $V_H$ domain or one $V_L$ domain, etc. $V_H$ and $V_L$ domains may be linked together via a synthetic linker to form various types of single-chain antibody designs in which the $V_H/V_L$ domains pair intramolecularly, or intermolecularly in those cases when the $V_H$ and $V_L$ domains are expressed by separate chains, to form a monovalent antigen binding site, such as single chain Fv (scFv) or diabody. In some embodiments, a polypeptide disclosed herein is an antigen binding fragment selected from Fab, F(ab')$_2$, Fab', scFv, or Fv. In some embodiments, the polypeptide is a scFv.

In some embodiments, a polypeptide disclosed herein (e.g., an antibody or antigen-binding fragment) is incorporated into a cell-based therapy. In some embodiments, the polypeptide is an engineered T cell receptor. In some embodiments, the polypeptide is a chimeric antigen receptor (CAR) (e.g., expressed on a T (CAR-T) cell, natural killer (CAR-NK) cell, or macrophage (CAR-M) cell). In some embodiments, the CAR comprises a transmembrane domain and an antigen-recognition moiety, wherein the antigen-recognition moiety binds SARS-CoV-2 (for example, an epitope within RBD, e.g., recognized by RBD Community 7).

In some embodiments, the polypeptide is an antibody mimetic. The term "antibody mimetic" refers to polypeptides capable of mimicking an antibody's ability to bind an antigen, but structurally differ from native single-chain antibody structures. Non-limiting examples of antibody mimetics include Adnectins, Affibodies, Affilins, Affimers, Affitins, Alphabodies, Anticalins, Avimers, DARPins, Fynomers, Kunitz domain peptides, monobodies, nanobodies, nanoCLAMPs, and Versabodies.

In some embodiments, a polypeptide disclosed herein further comprises an antibody heavy chain constant domain sequence. In some embodiments, the antibody heavy chain constant region is selected from the group consisting of an IgA constant region, an IgD constant region, an IgE constant region, an IgG constant region and an IgM constant region. In some embodiments, the IgG constant region is an IgG1 constant region, an IgG2 constant region, an IgG3 constant region or an IgG4 constant region. In some embodiments, the IgG2 constant region is an IgG2a, an IgG2b constant region or an IgG2c constant region. In some embodiments, the IgA constant region is an IgA1 constant region or an IgA2 constant region. In some embodiments, the antibody heavy chain constant region is an IgG1 constant region (e.g., IGHV5-51).

In some embodiments, a polypeptide disclosed herein further comprises an immunoglobulin light chain variable domain (V$_L$). The V$_H$ and V$_L$ domains may be linked together via a linker (e.g., a synthetic linker) to form various types of single-chain antibody designs in which the V$_H$/V$_L$ domains pair intramolecularly, or intermolecularly in those cases when the V$_H$ and V$_L$ domains are expressed by separate chains, to form a monovalent antigen binding site.

In some embodiments, the polypeptide further comprises an antibody light chain constant domain sequence. In some embodiments, the antibody light chain constant domain is selected from the group consisting of a κ constant domain and a λ constant domain. In some embodiments, the antibody heavy chain constant region is an IgG1 constant region, and the antibody light chain constant region is a κ constant region.

In some embodiments, the antibody heavy chain constant region sequence is at least about 60% identical to the amino acid sequence of SEQ ID NO: 12. For example, the antibody heavy chain constant region sequence can be at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 12. In some embodiments, the antibody heavy chain constant region sequence is at least about 70% or at least about 80% identical to the amino acid sequence of SEQ ID NO: 12. The sequence identified as SEQ ID NO: 12 is shown below:

```
                                            (SEQ ID NO: 12)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.
```

In some embodiments, the antibody light chain constant region sequence is at least about 60% identical to the amino acid sequence of SEQ ID NO: 13 or SEQ ID NO: 14. For example, the antibody light chain constant region sequence can be at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 13 or SEQ ID NO: 14. In some embodiments, the antibody light chain constant region sequence is at least about 70% or at least about 80% identical to the amino acid sequence of SEQ ID NO: 13 or SEQ ID NO: 14. The sequences identified as SEQ ID NO: 13 or SEQ ID NO: 14 are shown below:

```
                                            (SEQ ID NO: 13)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

(SEQ ID NO: 14)
GQPKANPTVTLFPPSSEELQANKATLVCLISDFYPGAVTVAWKADGSPVK

AGVETTKPSKQSNNKYAASSYLSLTPEQWKSHRSYSCQVTHEGSTVEKTV

APTECS.
```

In some embodiments, the antibody heavy chain constant region sequence comprises at least 1 amino acid substitution relative to the amino acid sequence of SEQ ID NO: 12. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the antibody heavy chain constant region sequence comprises about 1-10 amino acid substitutions, relative to the amino acid sequence of SEQ ID NO: 12.

In some embodiments, the antibody light chain constant region sequence comprises at least 1 amino acid substitution relative to the amino acid sequence of SEQ ID NO: 13 or SEQ ID NO: 14. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the antibody light chain constant region sequence comprises about 1-10 amino acid substitutions, relative to the amino acid sequence of SEQ ID NO: 13 or SEQ ID NO: 14.

In some embodiments, the amino acid substitutions are conservative substitutions. In some embodiments, the amino acid substitutions are highly conservative substitutions.

In some embodiments, a polypeptide disclosed herein is linked to a second polypeptide.

In some embodiments, the polypeptide and the second polypeptide are linked to each other via a linker. In some embodiments, the linker is a disulfide bond.

In some embodiments, the second polypeptide comprises a polypeptide described herein. In some embodiments, the second polypeptide comprises:
  a) a paratope that is identical to the paratope of a single-domain antibody comprising the amino acid sequence of SEQ ID NO: 3;
  b) a V$_H$ comprising a HCDR1, a HCDR2 and a HCDR3 that are identical to the HCDR1, HCDR2 and HCDR3, respectively, of a single-domain antibody comprising the amino acid sequence of SEQ ID NO: 3;
  c) a V$_H$ that is at least 85% identical to the amino acid sequence of SEQ ID NO: 3; or
  d) a V$_H$ comprising about 1-10 amino acid substitutions, relative to the amino acid sequence of SEQ ID NO: 3, or any combination of the foregoing.

In some embodiments:
  a) the polypeptide comprises the amino acid sequence of SEQ ID NO: 4 and the second polypeptide comprises the amino acid sequence of SEQ ID NO: 3, 4 or 5; or
  b) the polypeptide comprises the amino acid sequence of SEQ ID NO: 5 and the second polypeptide comprises the amino acid sequence of SEQ ID NO: 3, 4 or 5.

In some embodiments, the polypeptide comprises the amino acid sequence of SEQ ID NO: 4 and the second polypeptide comprises the amino acid sequence of SEQ ID NO: 3. In some embodiments, the polypeptide comprises the amino acid sequence of SEQ ID NO: 4 and the second polypeptide comprises the amino acid sequence of SEQ ID NO: 4. In some embodiments, the polypeptide comprises the amino acid sequence of SEQ ID NO: 4 and the second polypeptide comprises the amino acid sequence of SEQ ID NO: 5. In some embodiments, the polypeptide comprises the amino acid sequence of SEQ ID NO: 5 and the second polypeptide comprises the amino acid sequence of SEQ ID NO: 3. In some embodiments, the polypeptide comprises the amino acid sequence of SEQ ID NO: 5 and the second polypeptide comprises the amino acid sequence of SEQ ID NO: 4. In some embodiments, the polypeptide comprises the amino acid sequence of SEQ ID NO: 5 and the second polypeptide comprises the amino acid sequence of SEQ ID NO: 5.

In some embodiments, the polypeptide comprises the amino acid sequence of SEQ ID NO: 15 and the second polypeptide comprises the amino acid sequence of SEQ ID NO: 3. In some embodiments, the polypeptide comprises the amino acid sequence of SEQ ID NO: 15 and the second polypeptide comprises the amino acid sequence of SEQ ID NO: 4. In some embodiments, the polypeptide comprises the amino acid sequence of SEQ ID NO: 15 and the second polypeptide comprises the amino acid sequence of SEQ ID NO: 5. In some embodiments, the polypeptide comprises the amino acid sequence of SEQ ID NO: 15 and the second polypeptide comprises the amino acid sequence of SEQ ID NO: 15. In some embodiments, the polypeptide comprises the amino acid sequence of SEQ ID NO: 15 and the second polypeptide comprises the amino acid sequence of SEQ ID NO: 16. In some embodiments, the polypeptide comprises the amino acid sequence of SEQ ID NO: 16 and the second polypeptide comprises the amino acid sequence of SEQ ID NO: 3. In some embodiments, the polypeptide comprises the amino acid sequence of SEQ ID NO: 16 and the second polypeptide comprises the amino acid sequence of SEQ ID NO: 4. In some embodiments, the polypeptide comprises the amino acid sequence of SEQ ID NO: 16 and the second polypeptide comprises the amino acid sequence of SEQ ID NO: 5. In some embodiments, the polypeptide comprises the amino acid sequence of SEQ ID NO: 16 and the second polypeptide comprises the amino acid sequence of SEQ ID NO: 15. In some embodiments, the polypeptide comprises the amino acid sequence of SEQ ID NO: 16 and the second polypeptide comprises the amino acid sequence of SEQ ID NO: 16.

In some embodiments, the polypeptide, the second polypeptide, or both, are linked to a third polypeptide comprising a $V_L$.

In some embodiments, the third polypeptide further comprises an antibody light chain constant domain sequence. In some embodiments, the antibody light chain constant domain is selected from the group consisting of a κ constant domain and a λ constant domain.

In some embodiments, the antibody light chain constant region sequence is at least about 60% identical to the amino acid sequence of SEQ ID NO: 13 or SEQ ID NO: 14. For example, the antibody light chain constant region sequence can be at least about: 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the amino acid sequence of SEQ ID NO: 13 or SEQ ID NO: 14. In some embodiments, the antibody light chain constant region sequence is at least about 70% or at least about 80% identical to the amino acid sequence of SEQ ID NO: 13 or SEQ ID NO: 14.

In some embodiments, the antibody light chain constant region sequence comprises at least 1 amino acid substitution relative to the amino acid sequence of SEQ ID NO: 13 or SEQ ID NO: 14. For example, the number of amino acid substitutions can be at least about: 2, 3, 4, 5, 6, 7, 8, 9, 10, 11, 12, 13, 14, 15, 16, 17, 18, 19 or 20, or about: 1-20, 1-19, 2-19, 2-18, 2-17, 3-17, 3-16, 4-16, 4-15, 5-15, 5-14, 6-14, 6-13, 7-13, 7-12, 8-12, 8-11 or 9-11. In some embodiments, the antibody light chain constant region sequence comprises about 1-10 amino acid substitutions, relative to the amino acid sequence of SEQ ID NO: 13 or SEQ ID NO: 14. In some embodiments, the amino acid substitutions are conservative substitutions. In some embodiments, the amino acid substitutions are highly conservative substitutions.

In some embodiments, a polypeptide of the invention competes with a reference antibody for binding to the wildtype SARS-CoV-1-Spike, a SARS-CoV-1-Spike variant, or a combination thereof, wherein the reference antibody specifically binds the wildtype SARS-CoV-1-Spike. The term "specifically binding" or "specifically binds" refers to preferential interaction, i.e., significantly higher binding affinity, between an antibody, or an antigen-binding fragment thereof, and its epitope relative to other antigens or amino acid sequences.

In some embodiments, the reference antibody comprises a $V_H$ amino acid sequence of SEQ ID NO: 3. In some embodiments, the reference antibody comprises HCDR1, HCDR2 and HCDR3 amino acid sequences of SEQ ID NO: 6, SEQ ID NO: 7 and SEQ ID NO: 9, respectively.

In some embodiments, a polypeptide of the invention is an isolated polypeptide. In some embodiments, the isolated polypeptide is recombinantly produced. In some embodiments, the isolated polypeptide is synthetically produced.

In some embodiments, the polypeptide is conjugated to a heterologous moiety. The term "conjugated" refers to attached, via a covalent or noncovalent interaction. Conjugation can employ any of suitable linking agents. Non-limiting examples include peptide linkers, compound linkers, and chemical cross-linking agents.

In some embodiments, the heterologous moiety is a therapeutic agent, a diagnostic agent or a combination thereof. In some embodiments, the heterologous moiety is polyethylene glycol (PEG), hexadecanoic acid, hydrogels, nanoparticles, multimerization domains and carrier peptides.

In some embodiments, the nanoparticle is a lipid nanoparticle. In some embodiments, the nanoparticle is a polymer nanoparticle. In some embodiments, the polymer is an amphiphilic polymer. In other embodiments, the polymer is a hydrophobic or hydrophilic polymer. Non-limiting examples of polymers include poly(lactic acid)-poly(ethylene glycol), poly(lactic-co-glycolic acid)-poly(ethylene glycol), poly(lactic-co-glycolic) acid (PLGA), poly(lactic-co-glycolic acid)-d-α-tocopheryl polyethylene glycol succinate, poly(lactic-co-glycolic acid)-ethylene oxide fumarate, poly(glycolic acid)-poly(ethylene glycol), polycaprolactone-poly(ethylene glycol), or any salts thereof. In some embodiments, the polymer nanoparticle comprises poly(lactic-co-glycolic) acid (PLGA).

In some embodiments, the carrier polypeptide is albumin or an Fc polypeptide.

In some embodiments, a polypeptide of the invention:
a) is capable of binding to an epitope of SARS-CoV-2 RBD comprising amino acid residues corresponding to amino acid residues Y36, N37, S38, T39, F40, F41, S42, T43, F44, K45, C46, A51, T52, G71, D72, V74, R75, 1169, G170 and Y174 of SARS-CoV-1 RBD;
b) binds SARS-CoV-2 with an affinity of 10 μM or less;
c) reduces binding of SARS-CoV-2 to angiotensin-converting enzyme 2 (ACE2); or
d) reduces infectivity of SARS-CoV-2 in human cells, or a combination of any of the foregoing.

A non-limiting example of a wildtype SARS-CoV-1-Spike sequence is SEQ ID NO: 21.

(SEQ ID NO: 21)
NLCPFGEVFNATKFPSVYAWERKKISNCVADYSVLYNSTFFSTFKCYGVS

ATKLNDLCFSNVYADSFVVKGDDVRQIAPGQTGVIADYNYKLPDDFMGCV

LAWNTRNIDATSTGNYNYKYRYLRHGKLRPFERDISNVPFSPDGKPCTPP

ALNCYWPLNDYGFYTTTGIGYQPYRVVVLSFEGSLEVLFQ

In some embodiments, a polypeptide of the invention is capable of binding to an epitope of SARS-CoV-2 RBD comprising amino acid residues corresponding to amino acid residues Y36, N37, 538, T39, F40, F41, 542, T43, F44, K45, C46, A51, T52, G71, D72, V74, R75, 1169, G170 and Y174 of SARS-CoV-1 RBD. In certain embodiments, a polypeptide of the invention can also bind SARS-CoV1 RBD, e.g., amino acid residues Y36, N37, S38, T39, F40, F41, S42, T43, F44, K45, C46, A51, T52, G71, D72, V74, R75, 1169, G170 and Y174 of SARS-CoV-1 RBD.

In some embodiments, the polypeptide binds SARS-CoV-2-Spike with a binding constant ($K_D$) of about 10 μM or less. As used herein the term "$K_D$," also referred to as "binding constant," "equilibrium dissociation constant" or "affinity constant," is a measure of the extent of a reversible association between two molecular species (e.g., antibody and target protein) and includes both the actual binding affinity as well as the apparent binding affinity. Binding affinity can be determined using methods known in the art including, for example, by measurement of surface plasmon resonance, e.g., using a Biolayer interferometry (Octet, ForteBio) or a surface plasmon resonance (Biacore) system and assay. A reference that compares various surface technologies for measuring binding affinity and kinetics is Yang, D., Singh, A., Wu, H., & Kroe-Barrett, R., *Comparison of biosensor platforms in the evaluation of high affinity antibody-antigen binding kinetics*, Analytical Biochemistry 508: 78-96 (2016), the contents of which are incorporated herein by reference in their entirety.

In some embodiments, the polypeptide binds SARS-CoV-2-Spike with a $K_D$ of about: 5 μM, 2 μM, 1 μM, 500 nM, 200 nM, 100 nM, 50 nM, 20 nM, 10 nM, 5 nM, 2 nM, 1 nM, 0.5 nM, 0.2 nM or 0.1 nM or less. In some embodiments, the polypeptide binds SARS-CoV-2 with a $K_D$ of 100 nM or less.

In some embodiments, the polypeptide binds SARS-CoV-2-Spike with a $K_D$ of about: $10^{-10}$-$10^{-5}$ M, $10^{-10}$-$5\times10^{-6}$ M, $2\times10^{-10}$-$5\times10^{-6}$ M, $2\times10^{-10}$-$2\times10^{-6}$ M, $5\times10^{-10}$-$2\times10^{-6}$ M, $5\times10^{-10}$-$10^{-7}$ M, $10^{-9}$-$10^{-7}$ M, $10^{-9}$-$5\times10^{-8}$ M, $2\times10^{-9}$-$5\times10^{-8}$ M, $2\times10^{-9}$-$2\times10^{-8}$ M, $5\times10^{-9}$-$2\times10^{-8}$ M or $5\times10^{-9}$-$10^{-8}$ M.

In some embodiments, the polypeptide (e.g., camelid antibody) binds SARS-CoV-2-Spike or a fragment thereof (for example, an epitope within RBD, e.g., recognized by RBD Community 7) or a variant thereof with a $K_D$ of about $10^{-6}$ M or less, e.g., about: 500 nM, 200 nM, 100 nM, 50 nM, 20 nM, 10 nM, 5 nM, 2 nM, 1 nM, 0.5 nM, 0.2 nM or 0.1 nM or less; or about: $10^{-10}$-$10^{-6}$ M, $10^{-10}$-$5\times10^{-7}$ M, $2\times10^{-10}$-$5\times10^{-7}$ M, $2\times10^{-10}$-$2\times10^{-7}$ M, $5\times10^{-10}$-$2\times10^{-7}$ M, $5\times10^{-10}$-$10^{-7}$ M, $10^{-9}$-$10^{-7}$ M, $10^{-9}$-$5\times10^{-8}$ M, $2\times10^{-9}$-$5\times10^{-8}$ M, $2\times10^{-9}$-$2\times10^{-8}$ M, $5\times10^{-9}$-$2\times10^{-8}$ M or $5\times10^{-9}$-$10^{-8}$ M.

In some embodiments, the polypeptide binds SARS-CoV-1-Spike with a $K_D$ of about 10 μM or less. In some embodiments, the $K_D$ is about: 5 μM, 2 μM, 1 μM, 500 nM, 200 nM, 100 nM, 50 nM, 20 nM, 10 nM, 5 nM, 2 nM, 1 nM, 0.5 nM, 0.2 nM or 0.1 nM or less. In some embodiments, the polypeptide binds SARS-CoV-1-Spike with a $K_D$ of about: $10^{-10}$-$10^{-5}$ M, $10^{-10}$-$5\times10^{-6}$ M, $2\times10^{-10}$-$5\times10^{-6}$ M, $2\times10^{-10}$-$2\times10^{-6}$ M, $5\times10^{-10}$-$2\times10^{-6}$ M, $5\times10^{-10}$-$10^{-7}$ M, $10^{-9}$-$10^{-7}$ M, $10^{-9}$-$5\times10^{-8}$ M, $2\times10^{-9}$-$5\times10^{-8}$ M, $2\times10^{-9}$-$2\times10^{-8}$ M, $5\times10^{-9}$-$2\times10^{-8}$ M or $5\times10^{-9}$-$10^{-8}$ M.

In some embodiments, the polypeptide (e.g., camelid antibody) binds SARS-CoV-2-Spike or a fragment thereof (for example, an epitope within RBD, e.g., recognized by RBD Community 7) or a variant thereof with an association constant of about $10^6$/Ms or less, e.g., about: $5\times10^5$/Ms, $2\times10^5$/Ms, $10^5$/Ms, $5\times10^4$/Ms, $2\times10^4$/Ms, $10^4$/Ms or less; or about: $10^4$-$10^6$/Ms, $10^4$-$5\times10^5$/Ms, $2\times10^4$-$5\times10^5$/Ms, $2\times10^4$-$2\times10^5$/Ms, $5\times10^4$-$2\times10^5$/Ms or $5\times10^4$-$10^5$/Ms.

In some embodiments, the polypeptide (e.g., camelid antibody) binds SARS-CoV-2-Spike or a fragment thereof (for example, an epitope within RBD, e.g., recognized by RBD Community 7) or a variant thereof with a dissociation constant of about $10^{-2}$/s or less, e.g., about: $8\times10^{-3}$/s, $6\times10^{-3}$/s, $4\times10^{-3}$/s, $2\times10^{-3}$/s, $10^{-3}$/s, $8\times10^{-4}$/s, $6\times10^{-4}$/s, $4\times10^{-4}$/s, $2\times10^{-4}$/s, $10^{-4}$/s, $8\times10^{-5}$/s, $6\times10^{-5}$/s, $4\times10^{-5}$/s, $2\times10^{-5}$/s, $10^{-5}$/s, $8\times10^{-6}$/s, $6\times10^{-6}$/s, $4\times10^{-6}$/s, $2\times10^{-6}$/s or $10^{-6}$/s, or less; or about: $10^{-6}$-$10^{-2}$/s, $2\times10^{-6}$-$10^{-2}$/s, $2\times10^{-6}$-$5\times10^{-3}$/s, $5\times10^{-6}$-$5\times10^{-3}$/s, $5\times10^{-6}$-$2\times10^{-3}$/s, $10^{-5}$-$2\times10^{-3}$/s, $10^{-5}$-$10^{-3}$/s, $2\times10^{-5}$-$10^{-3}$/s, $2\times10^{-5}$-$5\times10^{-4}$/s, $5\times10^{-5}$-$5\times10^{-4}$/s, $5\times10^{-5}$-$2\times10^{-4}$/s or $10^{-4}$-$2\times10^{-4}$/s.

In some embodiments, the polypeptide (e.g., camelid antibody) binds SARS-CoV-2-Spike or a fragment thereof (for example, an epitope within RBD, e.g., recognized by RBD Community 7) or a variant thereof with a $R_{max}$ of about 0.05 or more, e.g., about: 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0 or more; or about: 0.1-2.0, 0.15-2.0, 0.15-1.8, 0.2-1.8, 0.2-1.6, 0.25-1.6, 0.25-1.4, 0.3-1.4, 0.3-1.2, 0.35-1.2, 0.35-1.0, 0.4-1.0, 0.4-0.95, 0.45-0.95, 0.45-0.9, 0.5-0.9, 0.5-0.85, 0.55-0.85, 0.55-0.8, 0.6-0.8, 0.6-0.75, 0.65-0.75 or 0.65-0.7.

In some embodiments, the polypeptide reduces binding of SARS-CoV-2-Spike to an entry receptor (e.g., ACE2). In some embodiments, the polypeptide competes with an entry receptor (e.g., ACE2) for binding to the S1 subunit receptor binding domain of SARS-Cov-2-Spike (RBD).

In some embodiments, the entry receptor is ACE2. In some embodiments, the ACE2 is a mammalian ACE2. In some embodiments, the ACE2 is a primate ACE2. In some embodiments, the primate ACE2 is human ACE2 (GeneID 59272; exemplary protein sequence NP_001358344.1). In some embodiments, the primate ACE2 is a non-human primate ACE2 selected from the group consisting of chimpanzee ACE2 (e.g., A0A2J8KU96, XP_016798468.1, XP_016798469.1, PNI38578.1), macaque ACE2 (e.g., B6DUF2, NP_001129168.1, XP_024647450.1), cynomolgus ACE2 (e.g., A0A2K5X283, XP_005593094.1) and combinations thereof.

In some embodiments, the polypeptide reduces binding of SARS-CoV-2-Spike to its cellular target receptor (e.g., ACE2) by at least about 10%. For example, by at least about: 15%, 20%, 25%, 30%, 35%0, 40%, 45%, 50%, 55%, 60%, 65%, 70%, 75%, 80%, 85%, 90%, 91%, 92%, 93%, 94%, 95%, 96%, 97%, 98% or 99%. In some embodiments, the polypeptide reduces binding of SARS-CoV-2-Spike to ACE2 by at least about 30%.

In some embodiments, the level of binding between SARS-CoV-2-Spike and its cellular target receptor (e.g., ACE2) in the presence of the polypeptide is less than about 90% relative to the level of binding in the absence of the polypeptide, for example, less than about: 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2% or 1%.

In some embodiments, the level of binding between SARS-CoV-2-Spike and its cellular target receptor (e.g., ACE2) in the presence of the polypeptide is about 1-90% relative to the level of binding in the absence of the polypeptide, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%, 15-45%, 15-40%, 20-40%, 20-35%, 25-35% or 25-30%, relative to the level of binding in the absence of the polypeptide.

In some embodiments, the polypeptide reduces binding of SARS-CoV-1-Spike to its cellular target receptor by at least about 10%. For example, by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

In some embodiments, the polypeptide (e.g., camelid antibody) neutralizes the SARS-CoV-2 infectivity of human host cells with an $IC_{50}$ of about 25,000 ng/mL or less, e.g., about: 20,000 ng/mL, 15,000 ng/mL, 10,000 ng/mL, 5,000 ng/mL, 2,500 ng/mL, 1,000 ng/mL, 750 ng/mL, 500 ng/mL, 250 ng/mL, 100 ng/mL, 75 ng/mL, 50 ng/mL, 25 ng/mL or 10 ng/mL or less; e.g., about: 10-25,000 ng/mL, 10-20,000 ng/mL, 25-20,000 ng/mL, 25-15,000 ng/mL, 50-15,000 ng/mL, 50-10,000 ng/mL, 75-10,000 ng/mL, 75-5,000 ng/mL, 100-5,000 ng/mL, 100-2,500 ng/mL, 250-2,500 ng/mL, 250-1,000 ng/mL, 500-1,000 ng/mL or 500-750 ng/mL.

In some embodiments, the polypeptide (e.g., camelid antibody) neutralizes the SARS-CoV-2 infectivity of human host cells with an $IC_{80}$ of about 50,000 ng/mL or less, e.g., about: 25,000 ng/mL, 15,000 ng/mL, 10,000 ng/mL, 5,000 ng/mL, 2,500 ng/mL, 1,000 ng/mL, 750 ng/mL, 500 ng/mL, 250 ng/mL, 100 ng/mL, 75 ng/mL, 50 ng/mL, 25 ng/mL or 10 ng/mL or less; e.g., about: 10-50,000 ng/mL, 10-25,000 ng/mL, 25-25,000 ng/mL, 25-15,000 ng/mL, 50-15,000 ng/mL, 50-10,000 ng/mL, 75-10,000 ng/mL, 75-5,000 ng/mL, 100-5,000 ng/mL, 100-2,500 ng/mL, 250-2,500 ng/mL, 250-1,000 ng/mL, 500-1,000 ng/mL or 500-750 ng/mL.

In some embodiments, the polypeptide reduces binding of SARS-CoV-2 to a host protease (e.g., the Type II transmembrane serine protease (TMPRSS2)). Without being bound to theory, the main host protease that mediates SARS-CoV-2-Spike activation on primary target cells and initial viral entry is TMPRSS2.

In some embodiments, the host protease is TMPRSS2. In some embodiments, the TMPRSS2 is a mammalian TMPRSS2. In some embodiments, the TMPRSS2 is a primate TMPRSS2, e.g., human TMPRSS2 or a non-human primate TMPRSS2 (e.g., chimpanzee TMPRSS2, macaque TMPRSS2 or cynomolgus TMPRSS2).

In some embodiments, the polypeptide reduces binding of SARS-CoV-2 to the host protease (e.g., TMPRSS2) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

In some embodiments, the level of binding between SARS-CoV-2 and the host protease (e.g., TMPRSS2) in the presence of the polypeptide is less than about 90% relative to the level of binding in the absence of the polypeptide, for example, less than about: 85%, 80%, 75%, 70%, 65%, 60%, 55%, 50%, 45%, 40%, 35%, 30%, 25%, 20%1, 15%, 0%, 9%, 8%, 7%, 6%, 5%, 4%, 3%, 2% or 1%.

In some embodiments, the level of binding between SARS-CoV-2 and the host protease (e.g., TMPRSS2) in the presence of the polypeptide is about 1-90% relative to the level of binding in the absence of the polypeptide, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%, 15-45%, 15-40%, 20-40%, 20-35%, 25-35% or 25-30%, relative to the level of binding in the absence of the polypeptide.

In some embodiments, the polypeptide reduces entry of SARS-CoV-2 into host cells (e.g., human host cells). In some embodiments, the polypeptide reduces entry of SARS-CoV-2 into host cells by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

In some embodiments, the polypeptide reduces infectivity of SARS-CoV-2 in host cells (e.g., human host cells). In some embodiments, the polypeptide reduces infectivity of SARS-CoV-2 in host cells (e.g., human host cells) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the polypeptide reduces infectivity of SARS-CoV-2 in human cells by at least about 30%.

In some embodiments, the polypeptide reduces re-infection of SARS-CoV-2 in host cells (e.g., human host cells). In some embodiments, the polypeptide reduces re-infection of SARS-CoV-2 in host cells (e.g., human host cells) by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the polypeptide reduces re-infection of SARS-CoV-2 in human cells by at least about 30%.

Infectivity or re-infection can be measured using techniques such as a pseudovirus neutralization assay or a live virus neutralization assay (see, e.g., Pinto et al., *Cross-neutralization of SARS-CoV-2 by a human monoclonal SARS-CoV antibody*, Nature 583: 290-95 (2020), the contents of which are incorporated herein by reference). A kit, for example, the GenScript cPass™ SARS-CoV-2 neutralization antibody detection kit (Genscript Biotech, Piscataway, NJ), can be used according to manufacturer's protocol.

In some embodiments, the host cells are selected from the group consisting of lung type II pneumocytes, ileal absorptive enterocytes, nasal goblet secretory cells, and combinations thereof.

Fusion Proteins

In another aspect, the invention provides a fusion protein comprising one or more of the polypeptides described herein.

The term "fusion protein" refers to a synthetic, semi-synthetic or recombinant single protein molecule. A fusion protein can comprise all or a portion of two or more different proteins and/or polypeptides that are attached by covalent bonds (e.g., peptide bonds). Fusion proteins of the invention can be produced recombinantly or synthetically, using routine methods and reagents that are well known in the art. For example, a fusion protein of the invention can be produced recombinantly in a suitable host cell (e.g., bacteria) according to methods known in the art. See, e.g., *Current Protocols in Molecular Biology*, Second Edition, Ausubel et al. eds., John Wiley & Sons, 1992; and *Molecular Cloning: a Laboratory Manual,* 2nd edition, Sambrook et al., 1989, Cold Spring Harbor Laboratory Press. For example, a nucleic acid molecule comprising a nucleotide sequence encoding a fusion protein described herein can be introduced and expressed in suitable host cell (e.g., *E. coli*), and the expressed fusion protein can be isolated/purified from the host cell (e.g., in inclusion bodies) using routine methods and readily available reagents. For example, DNA fragments coding for different protein sequences (e.g., a light-responsive domain, a heterologous peptide component) can be ligated together in-frame in accordance with conventional techniques. In another embodiment, the fusion gene can be synthesized by conventional techniques including automated DNA synthesizers. Alternatively, PCR amplification of nucleic acid fragments can be carried out using anchor primers that give rise to complementary overhangs between two consecutive nucleic acid fragments that can subsequently be annealed and re-amplified to generate a chimeric nucleic acid sequence (see Ausubel et al., Current Protocols in Molecular Biology, 1992).

Nucleic Acids, Expression Vectors, Expression Host Cells

In another aspect, the invention provides one or more polynucleotides encoding any one of the polypeptides or fusion proteins described herein. In some embodiments, the polypeptide or fusion protein of the invention is encoded by a single polynucleotide. In some embodiments, the polypeptide or fusion protein of the invention is encoded by multiple polynucleotides.

In some embodiments, the polynucleotide comprises a nucleotide sequence that is codon-optimized for a chosen host cell.

In another aspect, the invention provides an expression vector comprising any one or more of the polynucleotides described herein.

The term "expression vector" refers to a replicable nucleic acid from which one or more proteins can be expressed when the expression vector is transformed into a suitable expression host cell.

In some embodiments, the expression vector further comprises an expression control polynucleotide sequence operably linked to the polynucleotide, a polynucleotide sequence encoding a selectable marker, or both. In some embodiments, the expression control polynucleotide sequence comprises a promoter sequence, an enhancer sequence, or both. In some embodiments, the expression control polynucleotide sequence comprises an inducible promoter sequence. The term "promoter" refers to a region of DNA to which RNA polymerase binds and initiates the transcription of a gene. The term "operably linked" means that the nucleic acid is positioned in the recombinant polynucleotide, e.g., vector, in such a way that enables expression of the nucleic acid under control of the element (e.g., promoter) to which it is linked. The term "selectable marker element" is an element that confers a trait suitable for artificial selection. Selectable marker elements can be negative or positive selection markers.

In another aspect, the invention provides an expression host cell comprising any one or more of the polynucleotides or expression vectors described herein.

The term "expression host cell" refers to a cell useful for receiving, maintaining, reproducing and amplifying a vector. Non-limiting examples of expression host cells include mammalian cells such as hybridoma cells, Chinese hamster ovary (CHO) cells, COS cells, human embryonic kidney (HEK), yeast cells such as *Pichia pastoris* cells, or bacterial cells such as DH5a, etc.

Compositions

In another aspect, the invention provides a composition comprising any one of the polypeptides or fusion proteins described herein. In some embodiments, the composition is a pharmaceutical composition.

In some embodiments, the composition (e.g., pharmaceutical composition) further comprises pharmaceutically acceptable carriers, excipients, stabilizers, diluents or tonifiers (Remington's Pharmaceutical Sciences 16th edition, Osol, A. Ed. (1980)). Suitable pharmaceutically acceptable carriers, excipients, or stabilizers are nontoxic to recipients at the dosages and concentrations employed. Non-limiting examples of pharmaceutically acceptable carriers, excipients, stabilizers, diluents or tonifiers include buffers (e.g., phosphate, citrate, histidine), antioxidants (e.g., ascorbic acid or methionine), preservatives, proteins (e.g., serum albumin, gelatin or immunoglobulins); hydrophilic polymers, amino acids, carbohydrates (e.g., monosaccharides, disaccharides, glucose, mannose or dextrins); chelating agents (e.g., EDTA), sugars (e.g., sucrose, mannitol, trehalose or sorbitol), salt-forming counter-ions (e.g., sodium), metal complexes (e.g., Zn-protein complexes); non-ionic surfactants (e.g., Tween), PLURONICS™ and polyethylene glycol (PEG).

In some embodiments, the composition (e.g., pharmaceutical composition) of the invention is formulated for a suitable administration schedule and route. Non-limiting examples of administration routes include oral, rectal, mucosal, intravenous, intramuscular, subcutaneous and topical, etc. In some embodiments, the composition (e.g., pharmaceutical composition) of the invention is stored in the form of an aqueous solution or a dried formulation (e.g., lyophilized).

In some embodiments, the composition is formulated to be administered by infusion (e.g., intravenous infusion).

In some embodiments, the composition is formulated to be administered with a additional therapeutic agent(s) as a combination therapy.

Methods of Use

In another aspect, the invention provides a method of reducing the likelihood of a SARS-CoV-2 infection in a subject, comprising administering to the subject an effective amount of a pharmaceutical composition comprising a pharmaceutically acceptable carrier and, wherein as an active ingredient, any one of the polypeptides or fusion proteins described herein.

In some embodiments, the likelihood of SARS-CoV-2 infection in the subject is reduced by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%.

In some embodiments, the likelihood of SARS-CoV-2 infection in the subject in the presence of the polypeptide is about 1-90% relative to the likelihood in the absence of the polypeptide, for example, about: 2-90%, 2-85%, 3-85%, 3-80%, 4-80%, 4-75%, 5-75%, 5-70%, 6-70%, 6-65%, 7-65%, 7-60%, 8-60%, 8-55%, 9-55%, 9-50%, 10-50%, 10-45%1, 15-45%, 15-40%, 20-40%, 20-35%, 25-35% or 25-30%.

The term "subject" or "patient" refers to an animal (e.g., a mammal). A subject to be treated according to the methods described herein may be one who has been diagnosed with a particular condition (e.g., COVID-19), or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

In some embodiments, the subject has COVID-19. In some embodiments, the subject has been diagnosed with COVID-19. In other embodiments, the subject is at risk of developing COVID-19.

In some embodiments, the subject is a mammal. In some embodiments, the subject is a mammal selected from the group consisting of a dog, a cat, a mouse, a rat, a hamster, a guinea pig, a horse, a pig, a sheep, a cow, a chimpanzee, a macaque, a cynomolgus, and a human. In some embodiments, the subject is a primate. In some embodiments, the subject is a human.

In some embodiments, the subject has a heart disease. In some embodiments, the subject has a heart disease selected from the group consisting of a congenital heart disease, a coronary artery disease, a hypertensive heart disease, an inflammatory heart disease, a pulmonary heart disease, a rheumatic heart disease, a valvular heart disease, a cardiomyopathy, heart failure, and combinations thereof. In some embodiments, the subject has a congestive heart failure. In some embodiments, the subject has an inflammatory heart disease selected from the group consisting of endocarditis, cardiomegaly, myocarditis, and combinations thereof.

In some embodiments, the subject has diabetes.

In some embodiments, the subject has a lung disease. Non-limiting examples of lung diseases include acute respiratory distress syndromes, asthma, bronchitis, COPD, emphysema, lung tumors, pleural cavity diseases (e.g., pleural mesothelioma or tension pneumothorax), pulmonary vascular diseases (e.g., embolisms, edema, arterial hypertension or hemorrhage), respiratory tract infections (e.g., pneumonia or other upper or lower respiratory tract infections).

In some embodiments, the subject is a tobacco smoker.

In some embodiments, the subject is immune-compromised (e.g., has an underlying disorder or is on immunosuppressive therapy).

In some embodiments, the subject is 40 years or older, e.g., at least: 45, 50, 55, 60, 65, 70, 75, 80, 85, 90 years old.

"A therapeutically effective amount," "an effective amount" or "an effective dosage" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, a therapeutically effective amount may be administered in one or more administrations. A therapeutically effective amount may vary according to factors such as disease state, age, sex, and weight of a mammal, mode of administration and the ability of a therapeutic, or combination of therapeutics, to elicit a desired response in an individual.

An effective amount of an agent to be administered can be determined by a clinician of ordinary skill using the guidance provided herein and other methods known in the art. Relevant factors include the given agent, the pharmaceutical formulation, the route of administration, the type of disease or disorder, the identity of the subject (e.g., age, sex, weight) or host being treated, and the like. For example, suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment. Determining the dosage for a particular agent, subject and disease is well within the abilities of one of skill in the art. Preferably, the dosage does not cause or produces minimal adverse side effects.

Desired response or desired results include effects at the cellular level, tissue level, or clinical results. As such, "a therapeutically effective amount" or synonym thereto depends upon the context in which it is being applied. For example, in some embodiments it is an amount of the composition sufficient to achieve a treatment response as compared to the response obtained without administration of the composition. In other embodiments, it is an amount that results in a beneficial or desired result in a subject as compared to a control. As defined herein, a therapeutically effective amount of a composition of the present disclosure may be readily determined by one of ordinary skill by routine methods known in the art. Dosage regimen and route of administration may be adjusted to provide the optimum therapeutic response.

In some embodiments, the method is used for prophylactic therapy. In some embodiments, the effective dosage is sufficient to prevent the subject of being infected by SARS-CoV-2.

In some embodiments, the method is used for treating SARS-CoV-2 infection. The term "treating" or "treatment" refers to the medical management of a subject with the intent to improve, ameliorate, stabilize (i.e., not worsen), prevent or cure a disease, pathological condition, or disorder-such as the particular indications exemplified herein. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

In some embodiments, the effective dosage is sufficient to inhibit viral load in the subject. In some embodiments, the reduction in viral load is by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the reduction in viral load is about 10-99%, e.g., about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, the effective dosage is sufficient to reduce binding of the virus to its target proteins, target cells, or both. In some embodiments, the reduction in binding is by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the reduction in binding is about 10-99%, e.g., about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, the effective dosage is sufficient to inhibit virus mediated fusion with a target cell. In some embodiments, the reduction in fusion is by at least about 10%, e.g., by at least about: 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%. In some embodiments, the reduction in fusion is about 10-99%, e.g., about: 10-98%, 15-98%, 15-97%, 20-97%, 20-96%, 25-96%, 25-95%, 30-95%, 30-94%, 35-94%, 35-93%, 40-93%, 40-92%, 45-92%, 45-91%, 50-91%, 50-90%, 55-90%, 55-85%, 60-85%, 60-80%, 65-80%, 65-75%, or 70-75%.

In some embodiments, the effective dosage is sufficient to interfere with conformational changes in the viral envelope proteins necessary for cell infectivity.

A therapeutic agent described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound chosen.

In some embodiments, a polypeptide, composition, or pharmaceutical composition disclosed herein is administered to a subject in combination with one or more additional therapeutic agents (e.g., concurrently or sequentially with one or more additional therapeutic agents). In some embodiments, a subject has been previously treated with one or more therapeutic agents prior to being administered a polypeptide, composition, or pharmaceutical composition disclosed herein. In some embodiments, the method further comprises administering a therapeutically effective amount of one or more additional therapeutic agents to the subject at the same time as, or following administration of a polypeptide, composition, or pharmaceutical composition disclosed herein.

Non-limiting examples of additional therapeutic agents include antibiotics (e.g., azithromycin), antibodies or antigen-binding fragments thereof (e.g., other SARS-CoV-2-Spike-binding peptides), antimalarial agents (e.g., chloroquine or hydroxychloroquine), antiviral agents (e.g., favipiravir, lopinavir and/or ritonavir), cytokines (e.g., type 1 interferons such as interferon beta-1a), nucleotide analogs (e.g., remdesivir), protease inhibitors (e.g., danoprevir), Renin-Angiotensin-Aldosterone System Inhibitors (e.g., ACE2 inhibitors or angiotensin-receptor blockers (ARBs)).

In some embodiments, the antiviral agent is selected from the group consisting of amantadine, favipiravir, lopinavir, oseltamivir (Tamiflu), pleconaril, rimantadine, ritonavir, an anti-sense RNA to SARS-CoV-2, a siRNA to SARS-CoV-2, an additional anti-SARS-CoV-2 monoclonal antibody, and combinations thereof.

In some embodiments, the additional anti-SARS-CoV-2 monoclonal antibody targets the RBD of the S protein of SARS-CoV-2. In some embodiments, the additional anti-SARS-CoV-2 monoclonal antibody is a neutralizing monoclonal antibody. Non-limiting examples of anti-SARS-CoV-2 monoclonal antibodies include bamlanivimab (LY-CoV555 or LY3819253), etesevimab (LY-CoVO16 or LY3832479), casirivimab (REGN10933), and imdevimab (REGN10987). See, e.g., www.covid19treatmentguidelines.nih.gov/therapies/anti-sars-cov-2-antibody-products/anti-sars-cov-2-monoclonal-antibodies.

In some embodiments, the ACE2 inhibitor is selected from the group consisting of an RNAi to ACE2, a siRNA to ACE2, CRISPR-based inhibitor of ACE2, a soluble ACE2, a soluble ACE2 variant, an anti-ACE2 antibody, a vaccine, and combinations thereof. In some embodiments, the antibiotic is azithromycin. In some embodiments, the antimalarial agent comprises chloroquine or hydroxychloroquine. In some embodiments, the vaccine is a nucleic acid vaccine or an inactivated virus vaccine. In some embodiments, the vaccine is mrna-1273, BNT162, INO-4800, AZD1222, Ad5-nCoV, PiCoVacc, NVX-CoV2373, or a combination thereof.

Administration of the two or more therapeutic agents encompasses co-administration of the therapeutic agents in a substantially simultaneous manner, such as in a pharmaceutical combination. Alternatively, such administration encompasses co-administration in multiple containers, or separate containers (e.g., capsules, powders, and liquids) for each therapeutic agent. Such administration also encompasses use of each type of therapeutic agent in a sequential manner, either at approximately the same time or at different times. The composition described herein and the additional therapeutic agent(s) can be administered via the same administration route or via different administration routes.

In another aspect, the invention provides a method of preventing a SARS-CoV-2 infection in a subject, comprising administering to the subject an effective amount of a pharmaceutical composition comprising a pharmaceutically acceptable carrier and, wherein as an active ingredient, any one of the polypeptides or fusion proteins described herein.

In another aspect, the invention provides a method of treating a SARS-CoV-2 infection in a subject, comprising administering to the subject an effective amount of a pharmaceutical composition comprising a pharmaceutically acceptable carrier and, wherein as an active ingredient, any one of the polypeptides or fusion proteins described herein.

In another aspect, the invention provides a method of reducing viral load of SARS-CoV-2 in a subject, comprising administering to the subject an effective amount of a pharmaceutical composition comprising a pharmaceutically acceptable carrier and, wherein as an active ingredient, any one of the polypeptides or fusion proteins described herein.

In another aspect, the invention provides a method of inhibiting binding of SARS-CoV-2 to a target cell, comprising contacting the target cell an effective amount of any one of the polypeptides or fusion proteins described herein.

In another aspect, the invention provides a method of inhibiting binding of SARS-CoV-2 to a target protein on a target cell, comprising contacting the target cell an effective amount of any one of the polypeptides or fusion proteins described herein.

In another aspect, the invention provides a method of inhibiting virus mediated fusion with a target cell, comprising contacting the target cell an effective amount of any one of the polypeptides or fusion proteins described herein.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly-used dictionaries, should be interpreted as having a meaning that is consistent with their meaning in the context of the relevant art and/or as otherwise defined herein.

The terminology used herein is for the purpose of describing particular embodiments only and is not intended to be limiting.

As used herein, the indefinite articles "a," "an" and "the" should be understood to include plural reference unless the context clearly indicates otherwise.

Throughout this specification and the claims which follow, unless the context requires otherwise, the word "comprise," and variations such as "comprises" and "comprising", will be understood to imply the inclusion of, e.g., a stated integer or step or group of integers or steps, but not the exclusion of any other integer or step or group of integer or step. When used herein, the term "comprising" can be substituted with the term "containing" or "including."

As used herein, "consisting of" excludes any element, step, or ingredient not specified in the claim element. When used herein, "consisting essentially of" does not exclude materials or steps that do not materially affect the basic and novel characteristics of the claim. Any of the terms "comprising," "containing," "including," and "having," whenever used herein in the context of an aspect or embodiment of the invention, can in some embodiments, be replaced with the term "consisting of," or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and, therefore, satisfy the requirement of the term "and/or" as used herein. Concurrent applicability of more than one of the options is also understood to fall within the meaning, and, therefore, satisfy the requirement of the term "and/or."

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

EXEMPLIFICATION

Example 1. Direct Binding Between the Antigen-Binding Molecule and the S1 Subunit Receptor Binding Domain of SARS-Cov-2-Spike (RBD)

The molecule of interest is recombinantly expressed, purified, and quantified. An ELISA plate is coated with 1 µg/mL in PBS of commercial SARS-Cov-2 RBD overnight. The plate is then washed 3× with 200 µL of PBS-T on an automated plate washer and then blocked with 5% BSA in PBS for 1 hour at 37° C. to block non-specific binding. The plate is then washed 3× with 200 µL of PBS-T on an automated plate washer and the molecule of interest is titrated in a dilution series in the ELISA plate and incubated for 1 hour at 37° C. The plate is then washed 3× with 200 µL of PBS-T on an automated plate washer and a secondary antibody (conjugated with HRP) specific to the target molecule is added a fixed dilution to the plate. The plate is incubated for 1 hour at 37° C. The plate is then washed 3× with 200 µL of PBS-T on an automated plate washer and binding is probed with by adding TMB substrate to the wells of interest. After 5-10 minutes, the reaction is stopped with an acidic stop solution and the signal is quantified by measuring absorbance at 450 nm on a plate reader. A positive signal corresponds to an absorbance reading about background for a negative control (typically an antibody isotype control). A semi-quantitative understanding of the binding can be inferred by assessing strength of binding at greater dilutions of the target molecule. In theory, candidate molecules with greater affinity to the SARS-Cov-2 RBD should show greater signal at greater dilutions compared to weaker binders.

Example 2. The Antigen-Binding Molecule Competes with Human ACE2 (hACE2) for Binding to RBD In Vitro The molecule of interest is recombinantly expressed, purified, and quantified. An ELISA plate is coated with 1 µg/mL in PBS of commercial SARS-Cov-2 RBD overnight. The plate is then washed 3× with 200 µL of PBS-T on an automated plate washer and then blocked with 5% BSA in PBS for 1 hour at 37° C. to block non-specific binding. The plate is then washed 3× with 200 µL of PBS-T on an automated plate washer and the molecule of interest is titrated in a dilution series in the ELISA plate. At the same time, a fixed concentration of commercial hACE2 (biotinylated) is co-incubated with the candidate molecule. The fixed concentration of hACE2 corresponds to the concentration at which 50% of maximal binding to SARS-Cov-2 RBD determined empirically in this assay format. The plate is incubated for 1 hour at 37° C. The plate is then washed 3× with 200 µL of PBS-T on an automated plate washer and a secondary antibody (streptavidin conjugated with HRP) specific to the biotinylated hACE2 is added a fixed dilution to the plate. The plate is incubated for 1 hour at 37° C. The plate is then washed 3× with 200 µL of PBS-T on an automated plate washer and binding is probed with by adding TMB substrate to the wells of interest. After 5-10 minutes, the reaction is stopped with an acidic stop solution and the signal is quantified by measuring absorbance at 450 nm on a plate reader. A positive signal corresponds to a decrease in absorbance for wells with the candidate molecule compared to wells without the candidate molecule above background for a negative control (typically an antibody isotype control). A semi-quantitative understanding of the target molecule's ability to compete with hACE2 can be inferred by assessing total decrease of hACE2 binding at greater dilutions of the target molecule. In theory, candidate molecules with greater ability to compete with hACE2 for SARS-Cov-2 RBD should show greater signal at greater dilutions compared to molecules with weaker ability.

Example 3. The Antigen-Binding Molecule Competes with hACE2 for Binding to RBD on Cell Surface The molecule of interest is recombinantly expressed, purified, and quantified. A cell line expressing hACE2 at wild-type levels is cultured, harvested without trypsinization (to prevent surface protein destruction), and counted. A fixed number of cells are added to a 96 well plate and incubated with the molecule of interest titrated in a dilution series. At the same time, a fixed concentration of commercial SARS-Cov-2 (biotinylated) is co-incubated with the candidate molecule. The fixed concentration of SARS-Cov-2 corresponds to the concentration at which 50% of maximal binding to hACE2 on the cell determined empirically in this assay format. The plate of cells is incubated for 1 hour at 4° C. in the dark. The plate is centrifuged at 400×g for 5 minutes, the supernatant is aspirated, and the cells washed with 0.2% BSA in PBS. This process is repeated 2 more times for a total of 3 washes. A secondary antibody (streptavidin conjugated with Alexa Fluor 488) specific to the biotinylated SARS-Cov-2 is added a fixed dilution to the plate. The plate of cells is incubated for 1 hour at 4° C. in the dark. The plate is centrifuged at 400×g for 5 minutes, the supernatant is aspirated, and the cells washed with 0.2% BSA in PBS. The cells are then resuspended in a fixed volume of 0.2% BSA in PBS and subjected to flow cytometry. Total binding of the SARS-Cov-2 RBD is analyzed by median fluorescence intensity (MFI) of the FIT-C channel. A positive signal corresponds to a decrease in MFI for wells with the candidate molecule compared to wells without the candidate molecule above background for a negative control (typically an antibody isotype control). A semi-quantitative understanding of the ability to compete with SARS-Cov-2 RBD can be inferred by assessing total decrease of SARS-Cov-2 RBD MFI at greater dilutions of the target molecule. In theory, candidate molecules with greater ability to compete with the SARS-Cov-2 RBD for hACE2 (which can also be considered the affinity for SARS-Cov-2 RBD) should show greater signal at greater dilutions molecules with weaker ability.

Example 4. Yeast Display Characterization of Antibody Designs

Antibodies were formatted as a single VH domain fused to a c-Myc epitope tag and tested for binding using yeast display. VH-c-Myc fusion constructs were synthesized as DNA fragments (TWIST Biosciences), with overhangs for cloning into a yeast display vector. DNA insert and digested vector were transformed into yeast, and the full plasmid was generated in vivo by homologous recombination. Cells were induced for VH-c-Myc expression and display on the yeast cell surface. Induced cells were stained for binding to biotinylated SARS-CoV-2 receptor binding domain (RBD) antigen (ACROBiosystems, Newark, DE) or SARS-CoV RBD (Genscript) and anti-c-myc (Exalpha) for VHc-Myc expression. For clones that showed binding, the equilibrium dissociation constant ($K_D$) was evaluated by performing a titration curve with various concentrations of SARS-CoV-2 RBD or SARS-CoV antigen. All clones that bound SAR-CoV-2 RBD also demonstrated cross-reactive binding to SARS-CoV RBD. Binding specificity and $K_D$ values are summarized in Table 2.

Example 5. Production of VH-Fc Fusions

VH-cMyc fusion constructs were reformatted into VH-Fc fusions using conventional methods. Homodimeric VHH antibodies were generated by using an expression plasmid containing a CMV promoter to drive expression and a signal peptide to promote secretion of the fully folded VH-Fc fusion into the supernatant. Mammalian expression host systems (such as the Chinese hamster ovary—CHO S cell line) were employed for protein expression using cationic lipid-based transient transfection methodologies with fed-batch production procedures. The expressed, soluble VH-Fc fusions were purified using an affinity capture-based purification method using Protein A affinity resin (such as the MabSelect Sure resin, GE Healthcare) and aqueous buffers. Elution was performed under acidic conditions with low pH (such as pH 3.5) and then neutralized to pH7.5 using 2M Tris base. The purified VHH antibodies were further stabilized in aqueous buffers (such as Histidine-based buffers containing NaCl) for long-term storage/freezing.

Example 6. Binding Kinetics and Affinity of VHH Antibodies

Binding kinetics and affinity were measured with Bio-layer interferometry (BLI) using a ForteBio Octet Red96e instrument. Antibodies were captured onto biosensors. Biosensors were then incubated with a serial dilution of SARS-CoV-2 RBD (Acro Biosystems) for association and dissociation.

Example 7. Material and Methods

Expression of Full-Length IgG

Back-translated DNA coding for the VHH variable domain (scFc) sequences of designed antibodies were PCR amplified and cloned into a human hG1 Fc vector containing a CMV promoter sequence, signal peptide, and corresponding constant regions using NEBuilder® HiFi DNA Assembly (New England Biolabs, Ipswich, MA). VHH proteins were expressed in ExpiCHO cells following manufacturer's methods (Thermo Fisher Scientific, Inc., Waltham, MA) and purified by affinity chromatography using MabSelect Sure Protein A affinity resin (Cytiva, Marlborough, MA) per manufacturer's methods.

Neutralization Assay

Pre-titrated amounts of rVSV-SARS-CoV-2 were incubated with serially diluted monoclonal antibodies at 37° C. for 1 hour before addition to confluent Vero (ATCC CCL-81) monolayers in 96-well plates. Infection proceeded for 16-18 hours at 37° C. in 5% $CO_2$ before cells were fixed in 4% paraformaldehyde and stained with 10 μg/mL Hoechst. Cells were imaged using a CellInsight CX5 imager and infection was quantified by automated enumeration of total cells and those expressing green fluorescent protein (GFP). Infection was normalized to the average number of cells infected with rVSV-SARS-CoV-2 incubated with human IgG isotype control.

Generation of WT and Mutant SARS-CoV-2 Spike Proteins

Spike proteins were generated for epitope binning studies and structural biology using the HexaPro background (containing residues 14-1208 (Genbank: MN908947) of the ectodomain, six proline substitutions (F817P, A892P, A899P, A942P, K986P, V987P), as well as the D614G mutation established in all/most variants associated with spillover/spillback in Northern Europe, and replacement of cleavage site residues 682-685 ("RRAR" (SEQ ID NO: 18) to "GSAS" (SEQ ID NO: 19)). The resulting spike variants were cloned into a phCMV mammalian expression vector containing an N-terminal Gaussia luciferase signal sequence (MGVKVLFALICIAVAEA (SEQ ID NO: 20)) and a C-terminal foldon trimerization domain, followed by an HRV-3C cleavage site and a Twin-Strep-Tag. Plasmids were transformed into Stellar competent cells and isolated using a Plasmid Plus Midi kit (Qiagen, Hilden, Germany).

SARS-CoV-2 HexaPro spike was transiently transfected into Freestyle 293-F or ExpiCHO-S cells (Thermo Fisher Scientific, Inc., Waltham, MA). Both cell lines were maintained and transfected according to manufacturer's protocols. Briefly, 293-F cells were grown to a density of $2.0 \times 10^6$ cells/mL and diluted to $1.0 \times 10^6$ cell/mL on the day of transfection (day 0). Plasmid DNA and polyethyleneimine were mixed in Opti-MEM (Thermo Fisher Scientific, Inc., Waltham, MA), incubated for 25 minutes, and then added to the cells. Cell cultures were incubated at 37° C., 8% $CO_2$, and 120 RPM, and harvested on day 5. For ExpiCHO cultures, manufacturer's "High Titer" protocol was used. Briefly, cells were grown to a density of $1 \times 10^7$ cells/mL and diluted to $6 \times 10^6$ cells/mL on the day of transfection (day 0). Plasmid DNA and Expifectamine were mixed in Opti-PRO SFM (Thermo Fisher Scientific, Inc., Waltham, MA) according to manufacturer's instructions, and added to the cells. On day 1, cells were fed with manufacturer-supplied feed and enhancer according to the suggested protocol, and cultures were then incubated at 32° C., 5% $CO_2$ and 115 RPM. ExpiCHO cultures were harvested on day 7. All cultures were clarified by centrifugation, followed by addition of BioLock (IBA Lifesciences, Gottingen, Germany), and supernatants were flowed through a 0.22 μM sterile filter and purified on an AKTA GO (Cytiva, Marlborough, MA) using a 5 mL StrepTrap-HP column equilibrated with TBS buffer (25 mM Tris pH 7.6, 200 mM NaCl, 0.02% $NaN_3$) and eluted in TBS buffer supplemented with 5 mM d-desthiobiotin (Sigma-Aldrich, St. Louis, MO). The strep-tags were cleaved using HRV-3C protease, and the proteins were further purified by size-exclusion-chromatography (SEC) on a Superdex 6 increase 10/300 column (GE Healthcare, Chicago, IL) in TBS.

High-Throughput Surface Plasmon Resonance (HT-SPR) Epitope Binning

Epitope binning was performed with a sandwich assay format on a Carterra LSA SPR instrument equipped with a CMDP sensor chip at 25° C. and in a HBSTE-BSA running buffer (10 mM HEPES pH 7.4, 150 mM NaCl, 3 mM EDTA, 0.05% Tween-20, supplemented with 0.5 mg/ml BSA). Two microfluidic modules, a 96-channel print-head (96PH) and a single flow cell (SFC), were used to deliver samples onto the sensor chip. Surface preparation was performed with 25 mM MES (pH 5.5) with 0.05% Tween-20 as a running buffer. The chip was activated with a freshly prepared solution of 130 mM 1-ethyl-3-(3-dimethylaminopropyl)carbodiimide (EDC)+33 mM N-hydroxysulfosuccinimide (Sulfo-NHS) in 0.1 M MES (pH 5.5) using the SFC. Antibodies were immobilized using the 96PH for 10 minutes at 10 μg/mL diluted into 10 mM sodium acetate (pH 4.25). Unreactive esters were quenched with a 7-minute injection of 1 M ethanolamine-HCl (pH 8.5) using the SFC. The binning analysis was performed over this array with the HBSTE-BSA buffer as the running buffer and sample diluent. The RBD antigen was injected in each cycle for 4 minutes at 50 nM (1.3 μg/mL) and followed immediately by a 4-minute injection of the analyte antibody at 30 g/mL (200 nM for IgG constructs). The surface was regenerated each cycle with double pulses (17 seconds per pulse) of 10 mM Glycine (pH 2.0). The data was processed and analyzed with Epitope Tool software (Carterra, Salt Lake City, UT).

Example 8. Epitope and Affinities

The affinities of monoclonal antibodies against the soluble G614 HexaPro spike ectodomain and monomeric RBD were examined. Using a high-throughput surface plasmon resonance analysis, the antibodies that react with the RBD were sorted into 7 different "communities" (Coronavirus Immunotherapy Consortium (COVIC)). RBD communities were defined as the inability between two members of the same community to make SPR sandwich pairs, indicating a shared epitope for binding. It was found that Reference, AB-1 and AB-2 cluster into "RBD Community 7," a distinct "RBD community" epitope bin (COVIC, data not shown). Affinities to G614 HexaPro spike ectodomain and to monomeric RBD are described in Table 2.

Example 9. VHH Molecules Bind to SARS-COV-2 RBD by YSD

ScFv constructs fused to a c-myc epitope tag were synthesized as DNA fragments (Twist Biosciences) with overhangs for cloning into a yeast display vector. DNA inserts and digested vectors were transformed into yeast, and the full plasmid was generated in vivo by homologous recombination. Cells were induced for scFv expression and display on the yeast cell surface. Induced cells were stained for binding to biotinylated SARS-CoV-2 receptor binding domain (RBD) antigen (ACROBiosystems, Newark, DE) or SARS-CoV RBD (Genscript Biotech, Piscataway, NJ) and anti-c-myc (Exalpha Biologicals Inc, Shirley, MA) for scFv Expression. Affinity was determined by staining constructs at titrating concentrations of antigen and calculating $K_D$ at equilibrium by plotting median fluorescence intensity at each concentration (Table 2, FIG. 3).

Example 10. VHH Molecules Neutralize SARS-COV-2 In Vitro

AB-1 and AB-2 were submitted to the Coronavirus Immunotherapy Consortium (COVIC) for neutralization studies. Both molecules show the ability to block infection of Vero monolayers of both pseudo and authentic WT virus (Table 2).

Figure 4:
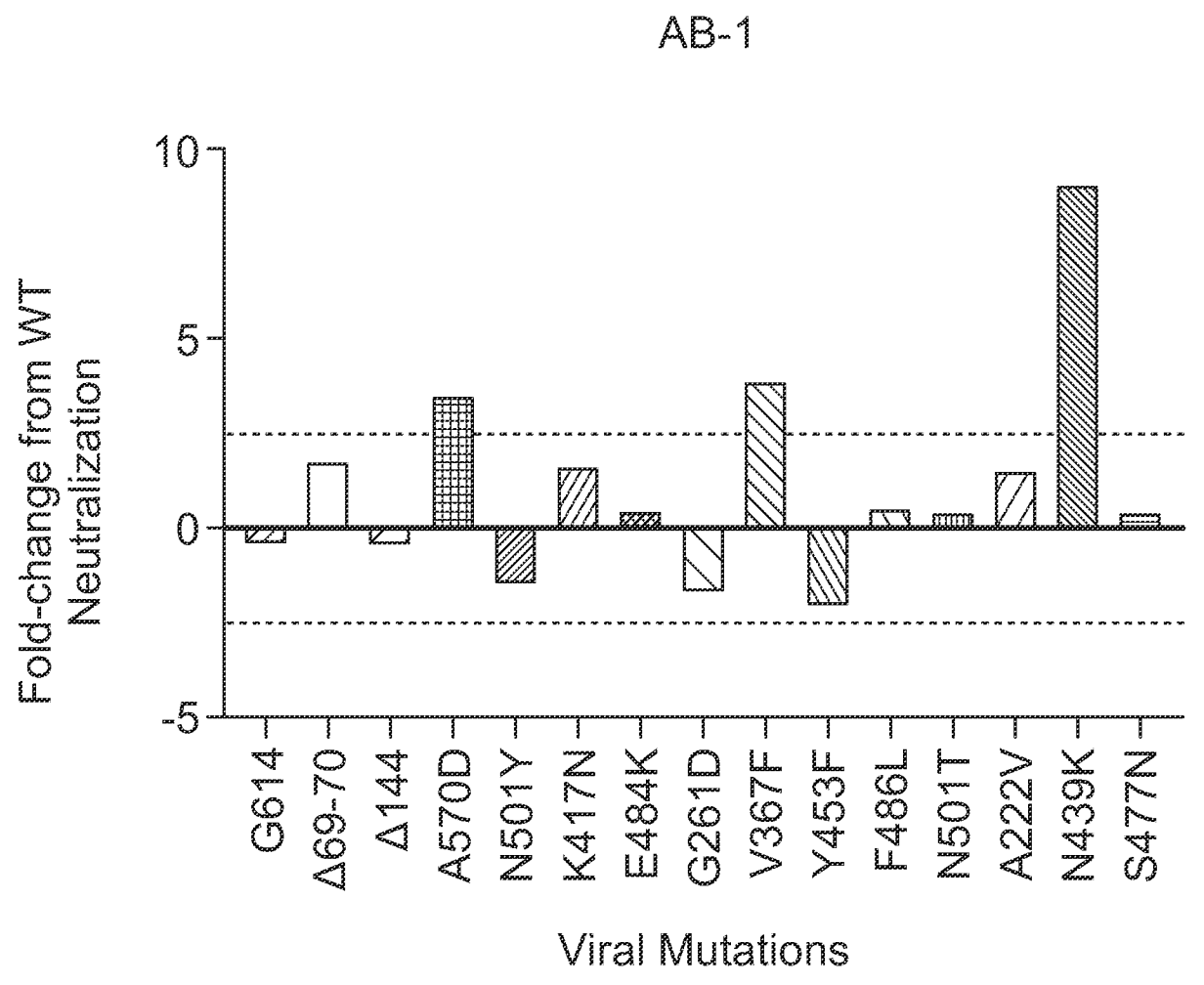

AB-1 was chosen to further investigate susceptibility of emerging mutations in COV-2 RBD. Pseudovirus neutralization studies were performed with pseudovirus bearing point mutations found in multiple human and mink variants. Data are presented in FIG. 4. AB-1 was resistant to most mutations as indicated by $IC_{50}$ fold-change between −2.5 and 2.5.

TABLE 1

Amino Acid Sequences

| Name | SEQ ID | Amino Acid Sequence |
|---|---|---|
| $V_H$ Consensus | NO: 2 | QVQLQESGGGLVQAGGSLRLSCAASGRTFSEYAMGWFRQAPGK EREFVATISWSGGSTYYTDSVKGRFTISRDNAKNTVYLQMNSL KPDDTAVYYCAAAGLGX$_1$X$_2$X$_3$SEWDYDYDYWGQGTQVTSSGS |

TABLE 1-continued

Amino Acid Sequences

| Name | SEQ ID | Amino Acid Sequence |
|---|---|---|
| V<sub>H</sub> Of Reference | NO: 3 | QVQLQESGGGLVQAGGSLRLSCAASGRTFSEYAMGWFRQAPGK EREFVATISWSGGSTYYTDSVKGRFTISRDNAKNTVYLQMNSL KPDDTAVYYCAAAGLGTVVSEWDYDYDYWGQGTQVTVSSGS |
| V<sub>H</sub> of AB-1 | NO: 4 | QVQLQESGGGLVQAGGSLRLSCAASGRTFSEYAMGWFRQAPGK EREFVATISWSGGSTYYTDSVKGRFTISRDNAKNTVYLQMNSL KPDDTAVYYCAAAGLGVVLSEWDYDYDYWGQGTQVTVSSGS |
| V<sub>H</sub> of AB-2 | NO: 5 | QVQLQESGGGLVQAGGSLRLSCAASGRTFSEYAMGWFRQAPGK EREFVATISYSGGSTYYTDSVKGRFTISRDNAKNTVYLQMNSL KPDDTAVYYCAAAGLGVHVSEWDYDYDYWGQGTQVTVSSGS |
| HCDR1 of Reference, AB-1, 2 | NO: 6 | GRTFSEYA |
| HCDR2 of Reference, AB-1, 2 | NO: 7 | ISWSGGST |
| HCDR3 Consensus | NO: 8 | AAAGLGX$_1$X$_2$X$_3$SEWDYDYDY |
| HCDR3 of Reference | NO: 9 | AAAGLGTVVSEWDYDYDY |
| HCDR3 of AB-1 | NO: 10 | AAAGLGVVLSEWDYDYDY |
| HCDR3 of AB-2 | NO: 11 | AAAGLGVHVSEWDYDYDY |
| Heavy Chain IgG1 | NO: 12 | ASTKGPSVFPLAPSSKSTSGGTAALGCLVKDYFPEPVTVSWNSGA LTSGVHTFPAVLQSSGLYSLSSVVTVPSSSLGTQTYICNVNHKPS NTKVDKKVEPKSCDKTHTCPPCPAPELLGGPSVFLFPPKPKDTLM ISRTPEVTCVVVDVSHEDPEVKFNWYVDGVEVHNAKTKPREEQ YNSTYRVVSVLTVLHQDWLNGKEYKCKVSNKALPAPIEKTISKA KGQPREPQVYTLPPSRDELTKNQVSLTCLVKGFYPSDIAVEWESN GQPENNYKTTPPVLDSDGSFFLYSKLTVDKSRWQQGNVFSCSVM HEALHNHYTQKSLSLSPGK |
| Light Chain κ | NO: 13 | RTVAAPSVFIFPPSDEQLKSGTASVVCLLNNFYPREAKVQWKVD NALQSGNSQESVTEQDSKDSTYSLSSTLTLSKADYEKHKVYACE VTHQGLSSPVTKSFNRGEC |
| Light Chain λ | NO: 14 | GQPKANPTVTLFPPSSEELQANKATLVCLISDFYPGAVTVAWKA DGSPVKAGVETTKPSKQSNNKYAASSYLSLTPEQWKSHRSYSCQ VTHEGSTVEKTVAPTECS |
| AB-1 | NO: 15 | QVQLQESGGGLVQAGGSLRLSCAASGRTFSEYAMGWFRQAPGK EREFVATISWSGGSTYYTDSVKGRFTISRDNAKNTVYLQMNSLK PDDTAVYYCAAAGLGVVLSEWDYDYDYWGQGTQVTVSSDKTH TCPPCPAPELLGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSREE MTKNQVSLTCLVKGFYPSDIAVEWESNGQPENNYKTTPPVLDSD GSFFLYSKLTVDKSRWQQGNVFSCSVMHEALHNHYTQKSLSLSP GK |
| AB-2 | NO: 16 | QVQLQESGGGLVQAGGSLRLSCAASGRTFSEYAMGWFRQAPGK EREFVATISYSGGSTYYTDSVKGRFTISRDNAKNTVYLQMNSLKP DDTAVYYCAAAGLGVHVSEWDYDYDYWGQGTQVTVSSDKTH TCPPCPAPELLGGPSVFLFPPKPKDTLMISRTPEVTCVVVDVSHED PEVKFNWYVDGVEVHNAKTKPREEQYNSTYRVVSVLTVLHQD WLNGKEYKCKVSNKALPAPIEKTISKAKGQPREPQVYTLPPSREE MTKNQVSLTCLVKGFYPSDIAVEWESNGQPENNYKTTPPVLDSD GSFFLYSKLTVDKSRWQQGNVFSCSVMHEALHNHYTQKSLSLSP GK |

Heavy Chain IgG1, Light Chain κ, Light Chain λ sequences are non-limiting example sequences.

TABLE 2

Yeast display affinity measurements

| Clone | YSD K$_D$ (nM) SARS-COV-2 RBD | YSD K$_D$ (nM) SARS-COV RBD | Octet K$_D$ (nM) |
|---|---|---|---|
| Reference | 6.0 | + | + |
| AB-1 | 9.3 | + | + |
| AB-2 | 6.6 | + | + |

REFERENCES

1. Baud D, et al. (2020) Real estimates of mortality following COVID-19 infection. *Lancet Infect Dis.*: S1473-3099(20)30195-X. doi: 10.1016/S1473-3099(20)30195-X. [Epub ahead of print].
2. Lindsey R. Baden and Eric J. Rubin (2020) Covid-19—The Search for Effective Therapy, *N Engl J Med.*, doi: 10.1056/NEJMe2005477.
3. Ziegler et al. (2020) SARS-CoV-2 receptor ACE2 is an interferon-stimulated gene in human airway epithelial cells and is detected in specific cell subsets across tissues, *Cell*, DOI: 10.1016/j.cell.2020.04.035 [Journal pre-proof].

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A polypeptide that specifically binds a severe acute respiratory syndrome coronavirus 2 Spike glycoprotein (SARS-CoV-2-Spike), comprising an immunoglobulin heavy chain variable domain ($V_H$) amino acid sequence comprising a heavy chain complementarity determining region 1 (HCDR1), a heavy chain complementarity determining region 2 (HCDR2) and a heavy chain complementarity determining region 3 (HCDR3) that are identical to the HCDR1, HCDR2 and HCDR3, respectively, of the amino acid sequence of SEQ ID NO: 4.

2. A polypeptide that specifically binds a severe acute respiratory syndrome coronavirus 2 Spike glycoprotein (SARS-CoV-2-Spike), comprising an immunoglobulin heavy chain variable domain ($V_H$) comprising the amino acid sequence of SEQ ID NO: 4.

3. The polypeptide of claim 1, wherein the $V_H$ comprises a heavy chain complementarity determining region 1 (HCDR1) comprising SEQ ID NO: 6, a heavy chain complementarity determining region 2 (HCDR2) comprising SEQ ID NO: 7, and a heavy chain complementarity determining region 3 (HCDR3) comprising SEQ ID NO: 10.

4. The polypeptide of claim 1, wherein the $V_H$ is at least 85% identical to the amino acid sequence of SEQ ID NO: 4.

5. The polypeptide of claim 3, wherein the $V_H$ comprises about 1-10 amino acid substitutions, relative to the amino acid sequence of SEQ ID NO: 4.

6. The polypeptide of claim 1, wherein the polypeptide is a single-domain antibody or an antigen-binding fragment thereof.

7. The polypeptide of claim 1, further comprising an antibody heavy chain constant domain sequence.

8. The polypeptide of claim 7, wherein the antibody heavy chain constant domain is selected from the group consisting of an IgA constant domain, an IgD constant domain, an IgE constant domain, an IgG constant domain and an IgM constant domain.

9. The polypeptide of claim 8, wherein the antibody heavy chain constant domain is an IgG1 heavy chain constant domain.

10. The polypeptide of claim 1, wherein the polypeptide is linked to a second polypeptide.

11. The polypeptide of claim 10, wherein the second polypeptide comprises the polypeptide of claim 3.

12. The polypeptide of claim 10, wherein the polypeptide comprises the amino acid sequence of SEQ ID NO: 4, and the second polypeptide comprises the amino acid sequence of SEQ ID NO: 3, 4 or 5.

13. The polypeptide of claim 10, wherein the polypeptide and the second polypeptide are linked to each other via a linker.

14. The polypeptide of claim 13, wherein the linker is a disulfide bond.

15. The polypeptide of claim 1, wherein the polypeptide is conjugated to a heterologous moiety.

16. The polypeptide of claim 1, wherein the polypeptide:
   a) binds SARS-CoV-2 with a $K_D$ of 10 µM or less;
   b) reduces binding of SARS-CoV-2 to angiotensin-converting enzyme 2 (ACE2); or
   c) reduces infectivity of SARS-CoV-2 in human cells, or any combination of the foregoing.

17. The polypeptide of claim 16, wherein the polypeptide binds SARS-CoV-2 with a $K_D$ of 100 nM or less.

18. The polypeptide of claim 16, wherein the polypeptide reduces binding of SARS-CoV-2 to ACE2 by at least about 30%.

19. The polypeptide of claim 16, wherein the polypeptide reduces infectivity of SARS-CoV-2 in human cells by at least about 30%.

20. A fusion protein comprising the polypeptide of claim 1.

21. A polynucleotide comprising a sequence encoding the polypeptide of claim 1.

22. An expression vector comprising the polynucleotide of claim 21.

23. A host cell comprising the polynucleotide of claim 21.

24. A composition comprising the polypeptide of claim 1 and one or more pharmaceutical excipients, diluents, or carriers.

25. The polypeptide of claim 1, wherein the $V_H$ comprises a heavy chain complementarity determining region 1 (HCDR1) consisting of SEQ ID NO: 6, a heavy chain complementarity determining region 2 (HCDR2) consisting of SEQ ID NO: 7, and a heavy chain complementarity determining region 3 (HCDR3) consisting of SEQ ID NO: 10.

26. The polypeptide of claim 1, wherein the polypeptide is a heavy-chain antibody.

27. The polypeptide of claim 1, wherein the polypeptide is a homodimeric $V_H$H antibody.

* * * * *

```
                        SEQUENCE LISTING

Sequence total quantity: 21
SEQ ID NO: 1            moltype = AA   length = 1273
FEATURE                 Location/Qualifiers
source                  1..1273
                        mol_type = protein
                        organism = Virus, Severe Acute Respiratory Syndrome
                        Coronavirus 2
SEQUENCE: 1
MFVFLVLLPL VSSQCVNLTT RTQLPPAYTN SFTRGVYYPD KVFRSSVLHS TQDLFLPFFS    60
NVTWFHAIHV SGTNGTKRFD NPVLPFNDGV YFASTEKSNI IRGWIFGTTL DSKTQSLLIV   120
NNATNVVIKV CEFQFCNDPF LGVYYHKNNK SWMESEFRVY SSANNCTFEY VSQPFLMDLE   180
GKQGNFKNLR EFVFKNIDGY FKIYSKHTPI NLVRDLPQGF SALEPLVDLP IGINITRFQT   240
LLALHRSYLT PGDSSSGWTA GAAAYYVGYL QPRTFLLKYN ENGTITDAVD CALDPLSETK   300
CTLKSFTVEK GIYQTSNFRV QPTESIVRFP NITNLCPFGE VFNATRFASV YAWNRKRISN   360
CVADYSVLYN SASFSTFKCY GVSPTKLNDL CFTNVYADSF VIRGDEVRQI APGQTGKIAD   420
YNYKLPDDFT GCVIAWNSNN LDSKVGGNYN YLYRLFRKSN LKPFERDIST EIYQAGSTPC   480
NGVEGFNCYF PLQSYGFQPT NGVGYQPYRV VVLSFELLHA PATVCGPKKS TNLVKNKCVN   540
FNFNGLTGTG VLTESNKKFL PFQQFGRDIA DTTDAVRDPQ TLEILDITPC SFGGVSVITP   600
GTNTSNQVAV LYQDVNCTEV PVAIHADQLT PTWRVYSTGS NVFQTRAGCL IGAEHVNNSY   660
ECDIPIGAGI CASYQTQTNS PRRARSVASQ SIIAYTMSLG AENSVAYSNN SIAIPTNFTI   720
SVTTEILPVS MTKTSVDCTM YICGDSTECS NLLLQYGSFC TQLNRALTGI AVEQDKNTQE   780
VFAQVKQIYK TPPIKDFGGF NFSQILPDPS KPSKRSFIED LLFNKVTLAD AGFIKQYGDC   840
LGDIAARDLI CAQKFNGLTV LPPLLTDEMI AQYTSALLAG TITSGWTFGA GAALQIPFAM   900
QMAYRFNGIG VTQNVLYENQ KLIANQFNSA IGKIQDSLSS TASALGKLQD VVNQNAQALN   960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                    1273

SEQ ID NO: 2            moltype = AA   length = 127
FEATURE                 Location/Qualifiers
REGION                  1..127
                        note = synthetic polypeptide
VARIANT                 103..105
                        note = Xaa can be any naturally occurring amino acid
source                  1..127
                        mol_type = protein
                        organism = synthetic construct
SEQUENCE: 2
QVQLQESGGG LVQAGGSLRL SCAASGRTFS EYAMGWFRQA PGKEREFVAT ISWSGGSTYY    60
TDSVKGRFTI SRDNAKNTVY LQMNSLKPDD TAVYYCAAAG LGXXXSEWDY DYDYWGQGTQ   120
VTVSSGS                                                             127

SEQ ID NO: 3            moltype = AA   length = 127
FEATURE                 Location/Qualifiers
REGION                  1..127
                        note = synthetic polypeptide
source                  1..127
                        mol_type = protein
```

```
                        organism = synthetic construct
SEQUENCE: 3
QVQLQESGGG LVQAGGSLRL SCAASGRTFS EYAMGWFRQA PGKEREFVAT ISWSGGSTYY    60
TDSVKGRFTI SRDNAKNTVY LQMNSLKPDD TAVYYCAAAG LGTVVSEWDY DYDYWGQGTQ   120
VTVSSGS                                                             127

SEQ ID NO: 4            moltype = AA  length = 127
FEATURE                 Location/Qualifiers
REGION                  1..127
                        note = synthetic polypeptide
source                  1..127
                        mol_type = protein
                        organism = synthetic construct
SEQUENCE: 4
QVQLQESGGG LVQAGGSLRL SCAASGRTFS EYAMGWFRQA PGKEREFVAT ISWSGGSTYY    60
TDSVKGRFTI SRDNAKNTVY LQMNSLKPDD TAVYYCAAAG LGVVLSEWDY DYDYWGQGTQ   120
VTVSSGS                                                             127

SEQ ID NO: 5            moltype = AA  length = 127
FEATURE                 Location/Qualifiers
REGION                  1..127
                        note = synthetic polypeptide
source                  1..127
                        mol_type = protein
                        organism = synthetic construct
SEQUENCE: 5
QVQLQESGGG LVQAGGSLRL SCAASGRTFS EYAMGWFRQA PGKEREFVAT ISYSGGSTYY    60
TDSVKGRFTI SRDNAKNTVY LQMNSLKPDD TAVYYCAAAG LGVHVSEWDY DYDYWGQGTQ   120
VTVSSGS                                                             127

SEQ ID NO: 6            moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 6
GRTFSEYA                                                              8

SEQ ID NO: 7            moltype = AA  length = 8
FEATURE                 Location/Qualifiers
REGION                  1..8
                        note = synthetic polypeptide
source                  1..8
                        mol_type = protein
                        organism = synthetic construct
SEQUENCE: 7
ISWSGGST                                                              8

SEQ ID NO: 8            moltype = AA  length = 18
FEATURE                 Location/Qualifiers
REGION                  1..18
                        note = synthetic polypeptide
VARIANT                 7..9
                        note = Xaa can be any naturally occurring amino acid
source                  1..18
                        mol_type = protein
                        organism = synthetic construct
SEQUENCE: 8
AAAGLGXXXS EWDYDYDY                                                  18

SEQ ID NO: 9            moltype = AA  length = 18
FEATURE                 Location/Qualifiers
REGION                  1..18
                        note = synthetic polypeptide
source                  1..18
                        mol_type = protein
                        organism = synthetic construct
SEQUENCE: 9
AAAGLGTVVS EWDYDYDY                                                  18

SEQ ID NO: 10           moltype = AA  length = 18
FEATURE                 Location/Qualifiers
REGION                  1..18
                        note = synthetic polypeptide
source                  1..18
                        mol_type = protein
                        organism = synthetic construct
```

```
SEQUENCE: 10
AAAGLGVVLS EWDYDYDY                                               18

SEQ ID NO: 11           moltype = AA  length = 18
FEATURE                 Location/Qualifiers
REGION                  1..18
                        note = synthetic polypeptide
source                  1..18
                        mol_type = protein
                        organism = synthetic construct
SEQUENCE: 11
AAAGLGVHVS EWDYDYDY                                               18

SEQ ID NO: 12           moltype = AA  length = 330
FEATURE                 Location/Qualifiers
source                  1..330
                        mol_type = protein
                        organism = Homo sapiens
SEQUENCE: 12
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 13           moltype = AA  length = 107
FEATURE                 Location/Qualifiers
source                  1..107
                        mol_type = protein
                        organism = Homo sapiens
SEQUENCE: 13
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 14           moltype = AA  length = 106
FEATURE                 Location/Qualifiers
source                  1..106
                        mol_type = protein
                        organism = Homo sapiens
SEQUENCE: 14
GQPKANPTVT LFPPSSEELQ ANKATLVCLI SDFYPGAVTV AWKADGSPVK AGVETTKPSK  60
QSNNKYAASS YLSLTPEQWK SHRSYSCQVT HEGSTVEKTV APTECS                106

SEQ ID NO: 15           moltype = AA  length = 352
FEATURE                 Location/Qualifiers
REGION                  1..352
                        note = synthetic polypeptide
source                  1..352
                        mol_type = protein
                        organism = synthetic construct
SEQUENCE: 15
QVQLQESGGG LVQAGGSLRL SCAASGRTFS EYAMGWFRQA PGKEREFVAT ISWSGGSTYY  60
TDSVKGRFTI SRDNAKNTVY LQMNSLKPDD TAVYYCAAAG LGVVLSEWDY DYDYWGQGTQ  120
VTVSSDKTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 16           moltype = AA  length = 352
FEATURE                 Location/Qualifiers
REGION                  1..352
                        note = synthetic polypeptide
source                  1..352
                        mol_type = protein
                        organism = synthetic construct
SEQUENCE: 16
QVQLQESGGG LVQAGGSLRL SCAASGRTFS EYAMGWFRQA PGKEREFVAT ISYSGGSTYY  60
TDSVKGRFTI SRDNAKNTVY LQMNSLKPDD TAVYYCAAAG LGVHVSEWDY DYDYWGQGTQ  120
VTVSSDKTHT CPPCPAPELL GGPSVFLFPP KPKDTLMISR TPEVTCVVVD VSHEDPEVKF  180
NWYVDGVEVH NAKTKPREEQ YNSTYRVVSV LTVLHQDWLN GKEYKCKVSN KALPAPIEKT  240
ISKAKGQPRE PQVYTLPPSR EEMTKNQVSL TCLVKGFYPS DIAVEWESNG QPENNYKTTP  300
PVLDSDGSFF LYSKLTVDKS RWQQGNVFSC SVMHEALHNH YTQKSLSLSP GK          352

SEQ ID NO: 17           moltype = AA  length = 209
FEATURE                 Location/Qualifiers
source                  1..209
                        mol_type = protein
                        organism = Virus, Severe Acute Respiratory Syndrome
```

```
                         Coronavirus 2
SEQUENCE: 17
RVQPTESIVR FPNITNLCPF GEVFNATRFA SVYAWNRKRI SNCVADYSVL YNSASFSTFK    60
CYGVSPTKLN DLCFTNVYAD SFVIRGDEVR QIAPGQTGKI ADYNYKLPDD FTGCVIAWNS   120
NNLDSKVGGN YNYLYRLFRK SNLKPFERDI STEIYQAGST PCNGVEGFNC YFPLQSYGFQ   180
PTNGVGYQPY RVVVLSFELL HAPATVCGP                                    209

SEQ ID NO: 18           moltype = AA   length = 4
FEATURE                 Location/Qualifiers
REGION                  1..4
                        note = synthetic polypeptide
source                  1..4
                        mol_type = protein
                        organism = synthetic construct
SEQUENCE: 18
RRAR                                                                  4

SEQ ID NO: 19           moltype = AA   length = 4
FEATURE                 Location/Qualifiers
REGION                  1..4
                        note = synthetic polypeptide
source                  1..4
                        mol_type = protein
                        organism = synthetic construct
SEQUENCE: 19
GSAS                                                                  4

SEQ ID NO: 20           moltype = AA   length = 17
FEATURE                 Location/Qualifiers
source                  1..17
                        mol_type = protein
                        note = copepod
                        organism = Gaussia princeps
SEQUENCE: 20
MGVKVLFALI CIAVAEA                                                   17

SEQ ID NO: 21           moltype = AA   length = 190
FEATURE                 Location/Qualifiers
source                  1..190
                        mol_type = protein
                        organism = Virus, Severe acute respiratory syndrome-related
                         coronavirus
SEQUENCE: 21
NLCPFGEVFN ATKFPSVYAW ERKKISNCVA DYSVLYNSTF FSTFKCYGVS ATKLNDLCFS    60
NVYADSFVVK GDDVRQIAPG QTGVIADYNY KLPDDFMGCV LAWNTRNIDA TSTGNYNYKY   120
RYLRHGKLRP FERDISNVPF SPDGKPCTPP ALNCYWPLND YGFYTTTGIG YQPYRVVVLS   180
FEGSLEVLFQ                                                         190
```